(12) United States Patent
Marasco et al.

(10) Patent No.: US 7,078,031 B2
(45) Date of Patent: Jul. 18, 2006

(54) PSEUDOTYPED LENTIVIRAL VECTORS AND USES THEREOF

(75) Inventors: Wayne A. Marasco, Wellesley, MA (US); Sandra Ogueta, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 54 days.

(21) Appl. No.: 10/844,873

(22) Filed: May 13, 2004

(65) Prior Publication Data

US 2005/0003505 A1 Jan. 6, 2005

Related U.S. Application Data

(60) Division of application No. 09/953,344, filed on Sep. 14, 2001, which is a continuation of application No. PCT/US00/06971, filed on Mar. 16, 2000.

(60) Provisional application No. 60/124,641, filed on Mar. 16, 1999.

(51) Int. Cl.
*A61K 48/00* (2006.01)
*C12N 15/867* (2006.01)
*C12N 15/63* (2006.01)
*C12N 15/64* (2006.01)

(52) U.S. Cl. ................ 424/93.2; 424/93.1; 424/93.6; 435/320.1; 435/455; 435/456

(58) Field of Classification Search ............. 435/320.1, 435/455, 456, 457; 424/93.1, 93.2, 93.6
See application file for complete search history.

(56) References Cited

U.S. PATENT DOCUMENTS

| 5,665,577 A | 9/1997 | Sodroski et al. |
| 5,981,276 A | 11/1999 | Sodroski et al. |
| 5,994,136 A | 11/1999 | Naldini et al. |
| 6,100,242 A * | 8/2000 | Hammond et al. ........... 514/44 |
| 6,864,227 B1 * | 3/2005 | Wang et al. .................. 514/2 |

FOREIGN PATENT DOCUMENTS

WO WO 99/51754 10/1999

* cited by examiner

*Primary Examiner*—David Guzo
(74) *Attorney, Agent, or Firm*—Nixon Peabody, LLP

(57) ABSTRACT

A vector system that will produce a pseudotyped lentiviral vector that can be used to deliver a desired gene is disclosed. The vector constructs that are described include a number of modifications that enhance the safety of the vector. The vector can be used to more specifically target cells for expression of certain genes.

3 Claims, 18 Drawing Sheets

TRANSFER VECTORS:

ATTENUATED HIV VECTOR (Δvif, nef, rev, vpr)

SELF-INACTIVATED HIV VECTOR

Tat-DELETED HIV VECTOR

PACKAGING CONSTRUCT:

pCMVgag-pol

VSV-G-CODING PLASMID:

pCMV-VSV-G

ACCESORY PLASMID:

Rev-CODING PLASMID

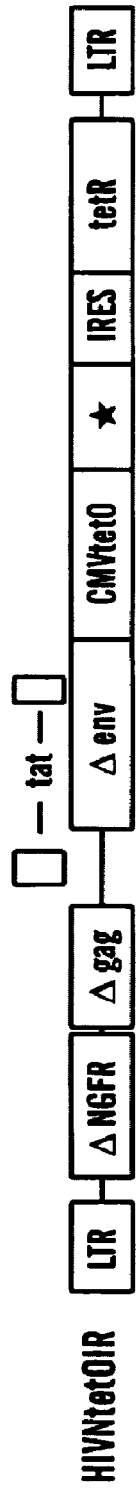
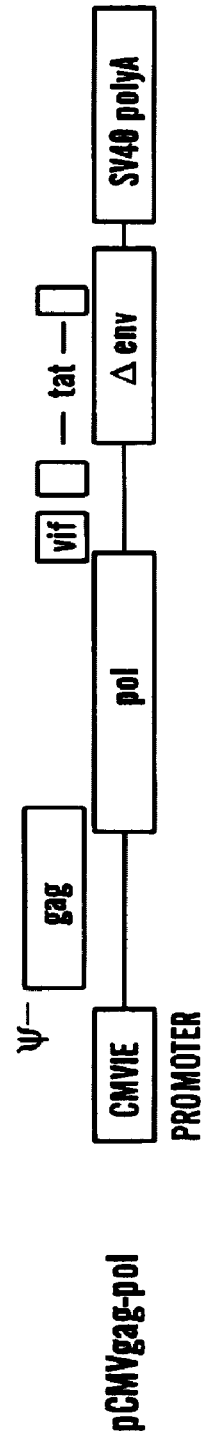
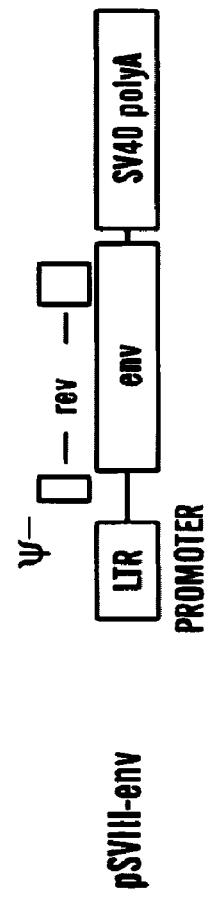
FIG. 5A
FIG. 5B

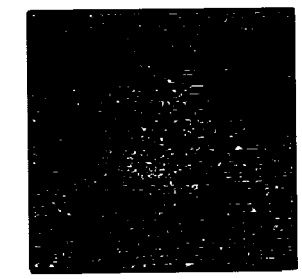
FIG. 11A
FIG. 11B
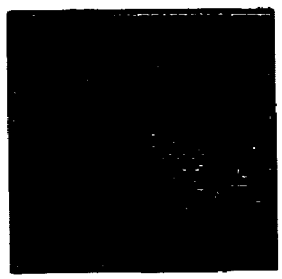
FIG. 11C
FIG. 11D
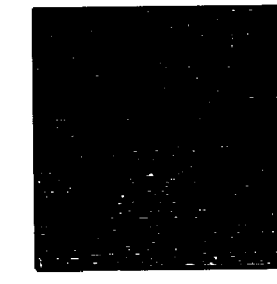
FIG. 11E
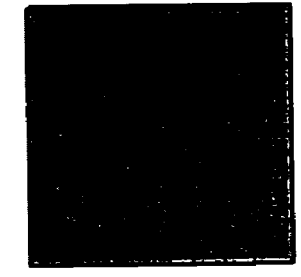
FIG. 11F
FIG. 11G
FIG. 11H

| VECTOR | INTERNAL PROMOTER | TAT EXPRESSION | % TOTAL FLUORESCENCE |
|---|---|---|---|
| HVPΔEB | + | + | 17 |
| HVPΔEB ΔLTR | + | + | 16.3 |
| HVPΔEB Δtat | + | − | 13.3 |
| HVPΔEB | − | + | 4.4 |
| HVPΔEB ΔLTR | − | + | 3.8 |
| HVPΔEB Δtat | − | − | 2.1 |

ALL THE REFERENCES DESCRIBED HEREIN ARE INCORPORATED BY REFERENCE.

*FIG. 18*

PSEUDOTYPED LENTIVIRAL VECTORS AND USES THEREOF

This application is a divisional of copending U.S. Ser. No. 09/953,344 filed Sep. 14, 2001, which was a continuation of PCT/US00/06971 filed Mar. 16, 2000, which designated the United States, and which also claimed benefit under 35 §U.S.C. 119(e) of 60/124,641 filed Mar. 16, 1999.

The present invention was funded in part by National Institutes of Health grants 5PO HL59316-02 and 5P30 AI 28691-10, and the U.S. Government has certain rights thereto.

FIELD OF THE INVENTION

The present invention is directed to a vector system wherein multiple lentiviral vectors are used to transfer nucleic acid segments to host cells. Preferably the system uses an inducible expression system to express the nucleic acid segments, and the lentiviral vectors are pseudotyped lentiviral vectors.

BACKGROUND OF THE INVENTION

In recent years considerable effort has been directed at applying gene delivery techniques. That term describes a wide variety of methods using recombinant biotechnology techniques to deliver a variety of different materials to a cell. These methods include, for example, vectors such as viral vectors, liposomes, naked DNA, adjuvant-assisted DNA, gene gun, catheters, etc. The different techniques used depend in part upon the gene being transferred and the purpose therefore. Thus, for example, there are situations where only a short-term expression of the gene is desired in contrast to situations where a longer term, even permanent expression of the gene is desired.

Vectors that have been looked at include both DNA viral vectors and RNA viral vectors. For example, DNA vectors include pox vectors such as orthopox or avipox vectors (see, e.g., U.S. Pat. No. 5,656,465), herpes virus vectors, such as herpes simplex I Virus (HSV) vectors [Geller, A. I. et al., *J. Neurochem.* 64:487 (1995); Lim, F., et al., *DNA Cloning: Mammalian Systems,* D. Glover, Ed., Oxford Univ. Press, Oxford, England (1995); Geller, A. I. et al., *Proc. Natl. Acad. Sci., U.S.A.* 90:7603 (1993)]: Adenovirus vectors [Legal Lasalle et al., *Sci.* 259–988 (1993); Davidson et al., *Nat. Genet.* 3:219 (1993); Yang et al., *J. Virol.,* 69:2004 (1995)]; and Adeno Associated Virus Vectors [Kaplitt, M. G., et al., *Nat. Genet.* 8;148 (1994)]. Retroviral vectors include Moloney murine leukemia viruses (MMLV) and human immunodeficiency viruses (HIV) [See, U.S. Pat. No. 5,665,577].

Recently, a great deal of attention has been focused on problems that may have arisen with clinical trials using gene delivery techniques. Many of the criticisms that have been raised do not address the value of such work, but rather failures to follow reporting procedures where adverse reaction and deaths occur. The individuals now receiving gene therapy are typically ill. Many have proved refractory to other treatment protocols. A number of these individuals have extremely poor life expectancies. Thus, as with other trials of patients in such poor health, problems can arise. It would be desirable to further improve gene delivery systems to reduce such problems.

Further, while attention has been focused on the use of viral vectors, particularly for in vivo therapy, for example, in somatic cell therapy or direct in vivo applications, many other applications exist such as in in vitro assays.

Various vectors have characteristics that make them desirable for certain applications. For example, a retroviral vector can be used to infect a host cell and have the genetic material integrated into that host cell with high efficiency. One example of such a vector is a modified Moloney murine leukemia virus (MMLV), which has had its packaging sequences deleted to prevent packaging of the entire retroviral genome. However, that retrovirus does not transduce resting cells. Additionally, since many retroviruses typically enter cells via specific receptors, if the specific receptors are not present on a cell or are not present in large enough numbers, the infection is either not possible or is inefficient. Concerns have also been expressed as a result of outbreaks of wild-type viruses from the recombinant MMLV producing cell lines, i.e., reversions.

An adenovirus vector can infect a wide range of cells. However, the transferred genetic material is not integrated. Therefore, it must be administered repeatedly. Additionally, most individuals have natural immunity to such vectors. Thus, high volumes of virus are needed when using the vector for gene delivery. The reason for this is the body's own immune system more readily attacks these vectors.

Recently, attention has focused on lentiviral vectors such as those based upon the primate lentiviruses, e.g., human immunodeficiency viruses (HIV) and simian immunodeficiency virus (SIV). HIV vectors can infect quiescent cells in addition to dividing cells. Moreover, by using a pseudotyped vector (i.e., one where an envelope protein from a different species is used), problems encountered with infecting a wide range of cell types can be overcome by selecting a particular envelope protein based upon the cell you want to infect. Additionally, in view of the complex gene splicing patterns seen in a lentiviruses such as HIV, multivalent vectors (i.e., those expressing multiple genes) having a lentiviral core, such as an HIV core, are expected to be more efficient. Yet, despite the advantages that HIV based vectors offer, there is still a concern with the use of HIV vectors in view of the severity of HIV infection. Thus, means for providing additional safeguards, such as attenuated forms that are less likely to revert to a wild type virus are desirable.

Variations can be made where multiple modifications are made, such as deleting nef. rev, vif and vpr genes. One can also have the 3' and 5' U3 deleted LTRs.

Marasco et al. discovered a method by which one could express antibodies within a cell and have them bind to a target within that cell. [See U.S. Pat. No. 5,851,829 to Marasco and Haseltine]. These intracellularly expressed antibodies (intrabodies) can be used in a method of functional genomics. In this manner, one can take a specific unknown gene, express its gene product, use that gene product to generate an antibody thereto and use the antibody intracellularly to "knock-out" the putative protein in the cell. Thereafter one can compare that cell to a control cell to determine the effect the loss of its gene product has on the cell in both in vitro and in vivo systems. This method requires generation of a specific antigen and antibody thereto. It would be desirable to have a method to take advantage of the efficiencies of this approach with large numbers of members of a particular group.

It would be highly desirable to have a vector and a method of use thereof where one could look for any molecule resulting in a particular function and rapidly determine that molecule, e.g. protein. It would be very desirable to be able to do this in an automated manner permitting rapid identification of the desired molecule.

SUMMARY OF THE INVENTION

We have now discovered a plurality of vectors, wherein the group of vectors can be used for gene delivery. The vectors preferably contain a heterologous nucleic acid sequence, preferably encoding proteins such as antibodies, angiogenic proteins, growth factors, receptors, cytokines, antiangiogenic proteins, co-stimulatory proteins, peptides, ribozymes and antisense molecules. Preferably the heterologous nucleic acid sequences are genes encoding proteins such as antibodies or angiogenic proteins. More preferably the nucleic acid sequences are operably linked to an inducible promoter. The vectors can be used to transduce a plurality of cells. Preferably, the vectors contains a marker gene to permit rapid identification and selection of transformed cells. Thereafter, those cells are screened to identify a cell exhibiting a desired phenotype. Cells exhibiting a desired phenotype are selected and the particular target molecule resulting in the phenotype identified.

In one preferred embodiment the plurality of vectors are lentiviral vectors. These lentiviral vectors preferably contain a selectable marker.

The lentivirus vectors include, for example, human immunodeficiency virus (HIV) (e.g. HIV-1 and HIV-2), feline immunodeficiency virus (FIV), or visna virus. A vector containing such a lentivirus core (e.g. gag) can transduce both dividing and non-dividing cells.

The lentiviral virion (particle) is expressed by a vector system encoding the necessary viral proteins to produce a virion (viral particle). Preferably, there is at least one vector containing a nucleic acid sequence encoding the lentiviral pol proteins necessary for reverse transcription and integration, operably linked to a promoter. Preferably, the pol proteins are expressed by multiple vectors. There is also a vector containing a nucleic acid sequence encoding the lentiviral gag proteins necessary for forming a viral capsid operably linked to a promoter. In one embodiment, the gag-pol genes are on the same vector. Preferably, the gag nucleic acid sequence is on a separate vector than at least some of the pol nucleic acid sequence, still more preferably it is on a separate vector from all the pol nucleic acid sequences that encode pol proteins.

In one embodiment, the gag sequence does not express a functional MA protein, i.e. the vector can still transduce cells in the absence of the entire MA or a portion thereof, if a myristylation anchor is provided. This can be accomplished by inactivating the "gene" encoding the MA by additions, substitutions or deletions of the MA coding region. Preferably, this is done by deletion. Preferably, at least 25% of the MA coding region is deleted, more preferably, at least 50% is deleted, still more preferably, at least 60%, even more preferably at least 75%, still more preferably, at least 90%, yet more preferably at least 95% and most preferably the entire coding region is deleted. However, in that embodiment, a myristylation anchor (sequence) is still required. Preferably, the myristylation sequence is a heterologous (i.e., non-lentiviral) sequence.

In another embodiment the lentiviral vector is another form of self-inactivating (SIN) vector as a result of a deletion in the 3' long terminal repeat region (LTR). Preferably, the vector contains a deletion within the viral promoter. The LTR of lentiviruses such as the HIV LTR contains a viral promoter. Although this promoter is relatively inefficient, when transactivated by e.g. tat, the promoter is efficient because tat-mediated transduction increases the rate of transcription about 100 fold. However, the presence of the viral promoter can interfere with heterologous promoters operably linked to a transgene. To minimize such interference and better regulate the expression of transgenes, the lentiviral promoter is preferably deleted.

Preferably, the vector contains a deletion within the viral promoter. The viral promoter is in the U3 region of the 3' LTR. A preferred deletion is one that is 120 base pairs between ScaI and PvuI sites, e.g. corresponding to nucleotides 9398–9518 of HIV-1 proviral clone HXO2, encompassing the essential core elements of the HIV-1 LTR promoter (TATA box, SP1 and NF—Pb binding sites). After reverse transcription, the deletion is transferred to the 5' LTR, yielding a vector/provirus that is incapable of synthesizing vector transcripts from the 5' LTR in the next round of replication. Thus, the vector of the present invention contains no mechanism by which the virus can replicate as it cannot express the viral proteins.

In another embodiment the vector is a tat deleted vector. This can be accomplished by inactivating at least the first exon of tat by known techniques such as deleting it or inserting a stop codon. Alternatively, one can extend the U3 LTR deletion into the R region to remove the TAR element.

Variations can be made where the lentiviral vector has multiple modifications as compared to a wildtype lentivirus. For example, with HIV being nef-, rev-, vpu-, vif- and vpr-. In addition one can have MA-gag, 3' and 5' U3 deleted LTR and variations thereof.

The vector(s) do not contain nucleotides from the lentiviral genome that package lentiviral RNA, referred to as the lentiviral packaging sequence. In HIV this region corresponds to the region between the 5' major splice donor and the gag gene initiation codon (nucleotides 301–319).

The env, gag and pol vector(s) forming the particle preferably do not contain a nucleic acid sequence from the lentiviral genome that expresses an envelope protein. Preferably, a separate vector that contains a nucleic acid sequence encoding an envelope protein operably linked to a promoter is used. This env vector also does not contain a lentiviral packaging sequence. In one embodiment the env nucleic acid sequence encodes a lentiviral envelope protein.

In another embodiment the envelope protein is not from the lentivirus, but from a different virus. The resultant particle is referred to as a pseudotyped particle. By appropriate selection of envelopes one can "infect" virtually any cell. Thus, the vector can readily be targeted to a specific cell. In Table A, a list of viruses and cell types that they preferentially infect is provided. Depending upon the host cell that one desires to target, one would take the envelope glycoprotein of that virus and use it as the envelope protein of the pseudotype vector. In another example, one can use an env gene that encodes an envelope protein that targets an endocytic compartment such as that of the influenza virus, VSV-G, alpha viruses (Semliki forest virus, Sindbis virus), arenaviruses (lymphocytic choriomeningitis virus), flaviviruses (tick-borne encephalitis virus, Dengue virus), rhabdoviruses (vesicular stomatitis virus, rabies virus), and orthomyxoviruses (influenza virus). In another embodiment, filoviruses are specific for vascular endothelium cells. Therefore, using an envelope glycoprotein such as $GP_1$, $GP_2$ from Ebola, one can selectively target vascular endothelium cells. When the desired host cell is a brain cell, the envelope glycoprotein from varicella zoster virus (VZV) can be used.

The envelope protein used can be a truncated protein as long as it retains the receptor binding site, which permit viral entry to a cell. Thus, for example, the cytoplasmic tail and/or transmembrane domains can be deleted.

The preferred lentivirus is a primate lentivirus [U.S. Pat. No. 5,665,577] or a feline immunodeficiency virus (FIV)

[Poeschla, E. M., et al., *Nat. Medicine* 4:354–357 (1998)]. The pol/gag nucleic acid segment(s) and the env nucleic acid segment will when expressed produce an empty lentiviral particle. By making the above-described modifications such as deleting the tat coding region the MA coding region, or the U3 region of the LTR, the possibility of a reversion to a wild type virus has been reduced.

A desired nucleic acid segment (sometimes referred to as the target molecule) such as a family of nucleic acid sequences can be inserted into the empty lentiviral particles by use of a plurality of vectors each containing a nucleic acid segment of interest and a lentiviral packaging sequence necessary to package lentiviral RNA into the lentiviral particles (the packaging vector). Preferably, the packaging vector contains a 5' and 3' lentiviral LTR with the desired nucleic acid segment inserted between them. The nucleic acid segment can be antisense molecules or more preferably, encodes a protein such as an antibody. The packaging vector preferably contains a selectable marker. These are well known in the art and include genes that change the sensitivity of a cell to a stimulus such as a nutrient, an antibiotic, etc. Genes include those for neo, puro, tk, multiple drug resistance (MDR), etc. Other genes express proteins that can readily be screened for such as green fluorescent protein (GFP), blue fluorescent protein (BFP), luciferase, LacZ, nerve growth factor receptor (NGFR), etc.

When an inducible promoter is used with the target molecule minimal selection pressure is exerted on the transformed cells for those cells where the target molecule is "silenced". Thus, identification of cells displaying the marker also identifies cells that can express the target molecule. If an inducible promoter is not used, it is preferable to use a "forced-expression" system where the target molecule is linked to the selectable marker by use of an internal ribosome entry site (IRES) [see Marasco et al., PCT/US96/16531].

IRES sequences are known in the art and include those from encephalomyocarditis virus (EMCV) [Ghattas, I. R. et al., *Mol Cell Biol.*, 11: 5848–5849 (1991)]; BiP protein [Macejak and Sarnow, *Nature*, 353:91 (1991)]; the Antennapedia gene of *Drosophila* (exons d and e) [Oh et al., *Genes & Dev.*, 6: 1643–1653 (1992)]; those in polio virus [Pelletier and Sonenberg, *Nature* 334:320325 (1988); see also Mountford and Smith, *TIG*, 11:179–184 (1985)]. Preferably, the target molecule is operably linked to an inducible promoter. Such systems allow the careful regulation of gene expression. See Miller, N. and Whelan, J., *Human Gene Therapy*, 8: 803–815 (1997). Such systems include those using the lac repressor from *E. coli* as a transcription modulator to regulate transcription from lac operator-bearing mammalian cell promoters [Brown, M. et al., *Cell*, 49:603–612 (1987)] and those using the tetracycline repressor (tetR) [Gossen. M., and Bujard, H., *Proc. Natl. Acad Sci. USA* 89:5547–5551 (1992); Yao. F. et al., *Human Gene Therapy*, 9:1939–1950 (1998); Shockelt, P., et al., *Proc. Natl. Acad Sci. USA.,* 92:6522–6526 (1995)]. Other systems include FK506 dimer VP16 or p65 using astradiol. RU486. diphenol murislerone or rapamycin [see Miller and Whelan, supra at FIG. 2]. Inducible systems are available from Invitrogen, Clontech and Arid. Systems using a repressor with the operon are preferred. Regulation of transgene expression in target cells represents a critical aspect of gene therapy. For example, a lac repressor combined the tetracycline repressor (tetR) with the transcription activator (VP16) to create a tetR-mammalian cell transcription activator fusion protein, tTa (tetR-VP16), with the tetO-bearing minimal promoter derived from the human cytomegalovirus (HCMV) major immediate-early promoter to create a tetR-tet operator system to control gene expression in mammalian cells. Recently Yao and colleagues [F. Yao et al., *Human Gene Therapy*, supra] demonstrated that the tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter. One particular advantage of this tetracycline inducible switch is that it does not require the use of a tetracycline repressor-mammalian cells transactivator or repressor fusion protein, which in some instances can be toxic to cells [M. Gossen et al., *Proc. Natl. Acad. Sci. USA*, 89: 5547–5551 (1992); P. Shockett et al., *Proc. Natl. Acad. Sci. USA*, 92:6522–6526 (1995)], to achieve its regulatable effects. Preferably, the repressor is linked to the target molecule by an IRES sequence. Preferably, the inducible system is a tetR system. More preferably the system has the tetracycline operator downstream of a promoter's TATA element such as with the CMVIE promoter. See FIG. 4.

The target molecules used in one embodiment have genes encoding antibodies intended to be expressed intracellularly. Antibodies have long been used in biomedical science as in vitro tools for the identification, purification and functional manipulation of target antigens. Antibodies have been exploited in vivo for diagnostic and therapeutic applications as well. Recent advances in antibody engineering have now allowed the gene encoding antibodies to be manipulated so that the antigen binding domain can be expressed intracellularly. The specific and high-affinity binding properties of antibodies, combined with the creation of large human immunoglobulin libraries and their ability to be stably expressed in precise intracellular locations inside mammalian cells, has provided a powerful new family of molecules for gene therapy applications. These intracellular antibodies are termed "intrabodies" [W. Marasco et al., *Gene Therapy*, 4:11–15 (1997)]. Preferably, the genes encode a single chain antibody. The molecules preferably contain a tag such as HA so that the molecule can be identified later.

The antibodies are preferably obtained from a library of antibodies such as a phage display library.

Thereafter the lentiviral vectors are used to transduce a host cell. One can rapidly select the transduced cells by screening for the marker. Thereafter, one can take the transduced cells and grow them under the appropriate conditions or insert those cells e.g. spleen cells or germ cells, into a host animal.

The promoter is induced and then one screens for cells and/or animals displaying a particular phenotype. Using the tag contained on the molecule, e.g. antibody, one can obtain the molecules, e.g., antibody that resulted in the desired phenotype. In one example, the antibody can then be used identify the antigen it bound to, if that is desired.

This method permits one to use a multitude of molecules to identify a specific molecule providing the desired function from a large group of molecules without first needing to know the specific identity of any member.

In another embodiment, the nucleic acid sequence encodes an angiogenesis promoting compound and is delivered selectively to vascular endothelial cells. To selectively target such cells, a pseudotyped lentiviral particle is used. The envelope is from a filovirus such as Ebola.

BRIEF DESCRIPTION OF THE DRAWINGS

FIG. 2A outline of the single inducible cassette and the expected polycistronic mRNA. FIG. 2B shows a Northern blot analysis. Mock-treated Vero cells and cells transfected independently with the empty vector, the pcDNAtetR plasmid, the one piece control (1Pc) and the one piece inducible (1Pi) were harvested after 2 days posttransfection and total RNA was separated using the TRIzol reagent, followed by chloroform extraction and precipitation with isopropanol. Total RNA (20 µg) was run in denaturing conditions and blotted on Hybond-N membranes to detect the presence of specific mRNAs that hybridize with a radiolabeled tetR probe (XbaI-EcoRI DNA fragment indicated in 2A). A transcript of about 0.6 Kb corresponding to the tetR mRNA is shown. Tetracycline regulation of the bicistronic mRNA expression from the inducible cassette is observed.

FIGS. 5A and B are a schematic of an HIV-1 based retroviral vector including a packaging vector, HIVNtetOIR, (FIG. 5A) and the packing defective lentiviral vectors (FIG. 5B).

FIG. 11A–H show co-expression of eGFP and tetR in transfected Vero cells. Vero cells transfected with 1Pc (FIGS. 11A–D) or 1Pi (FIGS. 11E–H) were grown for two days in the absence (FIGS. 11A, 11B, 11E and 11F) or presence (FIGS. 11C, 11D, 11G and 11H) of the inducer prior to analysis. Simultaneous observation of eGFP (FIGS. 11A, 11C, 11E and 11G) and tetR (FIGS. 11B, 11D, 11F and 11H) expression was performed by immuno-reaction of the tetR protein using a primary antibody against tetR and a secondary goat anti-mouse IgG coupled to PE that allows detection of the immune-complexes at different wavelengths.

(FIG. 13D) in the presence of tetracycline were fixed with 4% formaldehyde/PBS and permeabilized with a detergent before incubation with a monoclonal antibody against tetR. After 2 hr. incubation with the primary antibody, a goat anti-mouse IgG coupled to FITC allowed visualization under a fluorescence microscope (Final magnification 400×).

FIG. 18 illustrates results obtained with 6 constructs where three genetically modified HIV- I based vectors were tested for their ability to infect HeLa cells in vitro. The eGFP was used as reporter gene and gene expression driven from the internal CMV promoter or from the viral promoter itself evaluated by FACS analysis.

DETAILED DESCRIPTION OF THE INVENTION

Figure 1:
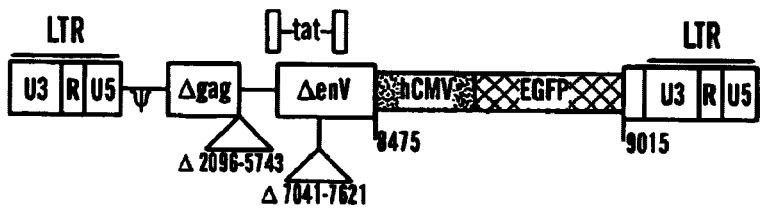
FIG. 1 provides a schematic of a lentiviral vector system.
Figure 1:
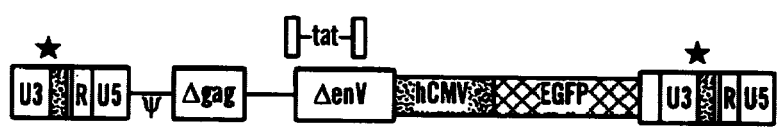
Figure 1:
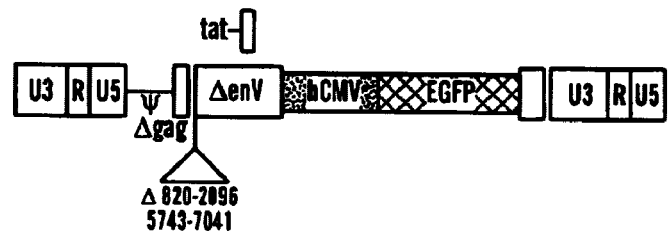
Figure 1:
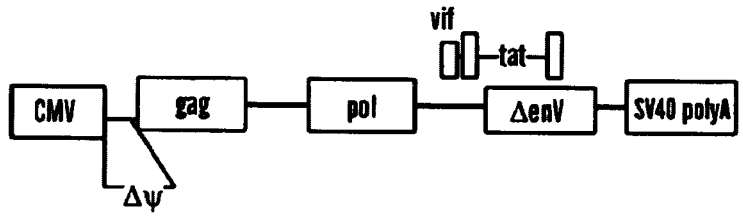
Figure 1:
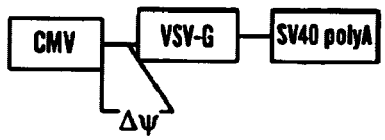

We have now discovered anew vector system using a plurality of vectors, wherein the group of vectors encode a lentiviral particle that can be used for gene delivery. Preferably, the lentiviral particles are pseudotyped having an envelope protein that differs from the lentiviral capsid. These particles can be used to transfer nucleic acid sequences. The molecules can be proteins such as antibodies, growth factors, angiogenic modulating proteins, receptors and cytokines, peptides, and antisense molecules. In one embodiment, the nucleic acid sequences are genes encoding proteins such as antibodies, or angiogenic promoting molecules. More preferably the proteins are operably linked to an inducible promoter. The vectors can be used to transduce a plurality of cells. In one alternative, the vectors contain a marker gene to permit rapid identification and selection of transformed cells. Thereafter, those cells are screened to identify a cell exhibiting a desired phenotype. Cells exhibiting a desired phenotype are selected and the particular target molecule resulting in a specific phenotype are identified.

In one preferred embodiment the plurality of vectors are lentiviral vectors. These lentiviral vectors preferably contain a selectable marker.

The lentivirus vectors include, for example, human immunodeficiency virus (HIV), feline immunodeficiency virus (FIV), or visna virus. A vector containing such a lentivirus core (e.g. gag gene) can transduce both dividing and non-dividing cells.

The preintegration complex of lentiviruses, a family of retroviruses which includes the human immunodeficiency virus type 1 (HIV-1), have been shown to possess nuclear targeting signals which allow these viruses to infect non-dividing cells including macrophages. The capacity of HIV-1 [P. Lewis et al., *EMBO J.*, 11 :3053–3058 (1992); M. Burinsky et al., *Proc. Natl. Acad. Sci. USA*, 89:6580–6584 (1992)] vectors to stably transduce non-dividing cells has been demonstrated in vitro [J. Reiser et al., *Proc. Natl. Acad. Sci. USA*, 93:15266–15271 (1996)] and also in vivo [L. Naldini et al., *Science*, 272:263–267 (1996)]. Thus, these vectors are capable of long-term expression.

A second feature of HIV-1 based vectors is the ability to manipulate the target cell range by substituting the HIV-1 envelope glycoprotein, gp160, with envelope proteins from other viruses which confer an extended host range that can be specifically targeted. The resultant particle is referred to as a pseudotyped particle. For example, robust association between the G protein of vesicular stomatitic virus (VSV)-G protein and the HIV-1 virion core allows virus particles to be concentrated without loss of infectivity and has enabled the production of HIV-1 vector stocks with titers of about $10^9$/ml [J. Reiser et al., *Proc. Natl Acad. Sci. USA,* 93:15266–15271 (1996); R. Akkina et al., *J. Virol.,* 70:2581–2585 (1996); J. Yee et al., *Proc. Natl. Acad. Sci. USA,* 91:9564–9568 (1994)]. Lentiviral vectors such as HIV-1 vectors have therefore been developed to a point of clinical utility and offer considerable potential as an in vivo tool for the manipulation of both dividing and non-dividing cells.

By appropriate selection of envelopes one can selectively “infect” virtually any cell. Table A provides a list of different viruses and cells that they infect. Using this information, one can readily choose a viral envelope protein to pseudotype in the present invention.

For example, filoviruses such as Ebola selectively infect vascular endothelial cells. These cells are involved in the circulatory system. Current protocols where circulatory problems exist involve administering an angiogenic protein such as vascular endothelial growth factor (VEGF) or basicFGF to adjoining cells to promote the growth of new blood cells. One method is to administer a gene encoding a protein such as an angiogenic protein, where the protein preferably has a secretory sequence. These genes are typically transferred to adjoining cells because it is difficult to transform the vascular endothelial cells. However, even where the method involves a gene delivery system such as a catheter, the transformation and expression of the angiogenic protein is not selective. While the individual having circulatory problems benefits by the expression of the angiogenic protein with respect to the circulatory problem, e.g., ischemia, that individual can be at increased risk from the undesired angiogenesis. One model of tumor growth suggests that it is the development of blood vessels near tumors that permit the tumor to grow and/or metastize. Thus, precise control over the targeting of cells and the expression of the protein is extremely important. An Ebola pseudotyped lentivirus provides such specific targeting, whereas the use of an inducible promoter as described later permits precision in expression.

In another example, one can use an env gene that encodes an envelope protein that targets an endocytic compartment such as that of the influenza virus, VSV-G, alpha viruses (Semliki forest virus, Sindbis virus), arenaviruses (lymphocytic choriomeningitis virus), flaviviruses (tick-borne encephalitis virus, Dengue virus), rhabdoviruses (vesicular stomatitis virus, rabies virus), and orthomyxoviruses (influenza virus).

Other envelopes that can preferably be used include those from Moloney Leukemia Virus such as MLV-E, MLV-A and GALV. These latter envelopes are particularly preferred where the host cell is a primary cell.

Other envelope proteins can be selected depending upon the desired host cell. For example, targeting specific receptors such as dopamine receptor for brain delivery. VZV will infect brain cells, ganglion cells and astrocytes.

TABLE A

| |
|---|
| <u>HSV</u> |
| Human diploid fibroblast, primary human embryonic kidney and primary rabbit kidney; Hep 2 Hela |
| <u>VZV</u> |
| Diploid fibroblasts, primary human kidney and primary monkey kidney |
| <u>CMV</u> |
| Human diploid fibroblasts. |
| <u>Influenza</u> |
| Primary monkey kidney cells; Madin - Darby kidney (MDCK) |
| <u>Paranfluenza</u> |
| Primary monkey kidney, human embryonic kidney cells |
| <u>Mumps</u> |
| Primary rhesus monkey kidney cells |
| <u>RSV</u> |
| Hep 2 cells |
| <u>Filoviruses</u> |
| Vascular endothelial |
| <u>Ad</u> |
| Human embryonic kidney (Hep 2) |
| <u>Rhinoviruses</u> |
| Human embryonic diploid Fb lines |
| <u>Measles</u> |
| Primary monkey kidney and primary human embryonic kidney cells |
| <u>Rubella</u> |
| 1° African green (vervet) monkey kidney cells |
| <u>HIV</u> |
| Macrophages, lymphocytes |
| <u>Arbovirus</u> |
| Embryonated eggs, chick embryo fibroblasts, some insect lines |

TABLE A-continued

II. IN DEPTH

Enteroviruses Eg Polio, Coxsackie, Echoviruses
Human TC = WI-38, HEK
Monkey kidney tissue culture
RD cell line (human rhabdomyosarcoma)
HeLa
Buffalo green monkey, primary human kidney cells
Human fetal diploid kidney cells
Poliovirus Primary monkey kidney cells, diploid Fibroblasts, Hep-2, HeLa, Vero
Coxsackie B, A & Echovirus CBV = Primary kidney cells from monkeys
or human embryos; Hep-2, HeLa Vero
CAV = inoculation of newborn mice
Echo = Primary monkey and human embryo kidney;
human diploid fibroblast cell lines
Rhinoviruses Rhesus monkey kidney cell lines.
Human embryonic kidney cells; human amnion; diploid fibroblasts
from human embryonic lung, tonsil, liver,
intestine and skin.
adult fibroblast cell lines from aorta and gingiva
L132, KB, Hep-2, and HeLa (transformed cells); WI-38 (diploid
Fibroblast), fetal tonsil line (Cooney strain);
MRC-5 line
Hepatitis
HAV Primary explant cultures of marmoset liver
Fetal rhesus monkey kidney cell line (FRhK6)
Primary African green monkey kidney cells (AGMK),
Primary human fibroblast cells.
Transformed human diploid lung cells (MRC5)
Cell lines derived from: (I) AGMK = BS-C-1, Vero, BGMK
fetal rhesus kidney = FRhK4, FRhK6, Frp/3
Human hepatoma = PLC, PRf/5
HBV 1° cultures of normal adult or fetal human hepatocytes tissue = liver
Hepatitis E Diploid human embryonic lung cells, 1° cynomolgus
monkey hepatocyte culture
Host range depends on several genes
Norwalk Not propagated in cell culture or in human
embryonic intestinal organ culture
Astroviruses Tertiary bovine embryo kidney cells (BEK)
Primary neonatal bovine kidney cells (NBK)
Togavirus Chicken embryo fibroblasts (CEF)
Baby hamster kidney cells (BHK)
Alphaviruses Avian embryo cells
Continuous cell lines = baby hamster kidney (BHK-21); monkey
kidney (Vero) and mosquito (C6/36)
Rubella Rabbit kidney line RK-13, AGMK, Vero, BHK-21 Baby hamster kidney
Flavivirus primary chick or duck embryonic cells.
Grow in continuous cell cultures from human, monkey,
rodent, swine avian, amphibian and anthropod.
HeLa, BHK-21, porcine kidney (PS), SW-13 (human
adrenal carcinoma), Aedes mosquito cells
Filoviruses Ebola
Tropic for vascular endothelial cells

TABLE A-continued

Pestiviruses

Can be propagated in cultures of primary and permanent cells of their
host species eg. deer, african buffalo,
giraffe, wildebeest, most pigs, cattle, sheep, goats
Coronavirus None of human coronavirus grow well in cell culture
without extensive adaptation by passage.
Some grown in human embryonic tracheal organ
culture, primary or secondary
human fibroblast cell lines (HEK).
Most sensitive is diploid intestinal cell line MA-177.
Fetal tonsil diploid cells (FT)
Rhadovirus BHK-21, Vero, primary chick embryo cells, Chinese
hamster ovary cells, fish cell lines.
Filoviridae Passaged in Monkeys, guinea pigs, suckling mice and hamsters.
Cell culture: vero cells (clone E-6), MA-108,
SW-13, NIH-3T3, BSC-1 MDCK HeLa.
Paranfluenza Embryonated chicken eggs, monkey kidney cells.
Mumps Virus Primary rhesus monkey kidney cells, BSC-1, Vero, MDBK, HeLa
Measles Virus Peripheral blood leukocytes or respiratory secretions inoculated onto
primary human or monkey kidney cells;
human cord blood leukocytes.
Cell cultures: Vero, CV-1 (continuous monkey kidney cell line) EBV
transformed marmoset B lymphocyte line;
B95-8; A549 cells
Respiratory Syncytial Virus (RSV)

Hep-2, HeLa, wide variety of human and animal cells
Orthomyxvirus eg. Influenza

MDCK, primary cell cultures including monkey kidney,
calf kidney, hamster kidney and chicken kidney
Bunyaviridae Most cell cultures
Arenaviridae eg LCMV Most cell types from many different host species but not
lymphocytes and terminally differentiated neurons
Reoviridue MDCK, 3T3 (primary fibroblasts)
Reoviruses Mouse L929 fibroblasts, Madin-Darby bovine kidney
(MDBK) rhesus monkey (LLC-MK2) human
embryonic intestinal cells
Rotaviruses Bovine RV = Bovine kidney cells, BSC-1,
polarized human intestinal epithelial (CaCO-2)
Rhesus RV = MDCK, CaCO-2
HTLV T cells, human cord or PBL's, EBV-transformed B cell lines,
B cells, immature cells from bone marrow which do
not have T-cell phenotype; macrophages, cells of neural origin
Growth in vitro (I) HTLV-I = $CD4^+CD8^-$
(ii) HTLV-II = $CD8^+$
Polyomaviruses Vero cells; epithelial and fibroblastic cells of human origin,
HEK, diploid lung fibroblasts (WI38), urothelial cells,
primary human fetal glial (PHFG) Human fetal
Schwann cells (glial lineage), human fetal astrocytes, HEK TABLE A-continued Papillonaviruses Not successfully propagated in
monolayer cell culture to yield virus particles
Adenovirus Best grown in human embryonic kidney cells (HEK)
A549 - derived from a human lung carcinoma
Hep-2, HeLa, KB, monkey kidney cells lines eg. Vero
293 cell line - primary HEK transformed by Ad5 (EIA&B positive) cells
primary monkey kidney cells
Parvovirus Human erythroid cells and cultures of human bone marrow,
peripheral blood leukocytes, immuophenotype of cells
infected = surface expression of glycophorins, HLA,
leucosialin (CD43) andplatelet glycoprotein IV (CD36)
HSV Vero, Hep-2, baby hamster kidney cells
EBV B cells, EBV positive malignant cells BL (Burkitt cells)
In vivo = permissive in pharyngeal epithelium.
Immunophenotype of BL cells: BL group 1 = CD10, CD77
BL group III CD23, CD30, CD39, CD70, B7, LFA3, ICAM1
CMV Found in virtually all organ systems.
Varicella Zoster virus VZV found in thyroid, human melanoma,
human embryo lung fibroblast etc.
Grows in primary diploid and continuous human cell cultures
such as primary human foreskin fibroblasts, kidney,
thyroid, amnion cells, primary human keratinocytes,
adult brain cells, ganglion cells, astrocytes, Schwanncells
VZV can be propagated in W1-38 or MRC-5 cells
Infects a human neuroblastoma cell line (IMR-32)
Replicates in EBV-transformed human B lymphocytes in vitro
Infects activated T cells in vitro
Grows in primary rhesus monkey kidney cells, African
green monkey kidney cells, guinea pig embryo fibroblasts.
Primate cell lines - BSC-1 and Vero
Human Herpesvirus 6

Cell tropism = CD4$^+$ T cells
in vitro = primary human monoyte/macrophage, NK cells,
megakaryocytes, glial cell lineages and transformed
cervical epithelial cells, Molt-3 (T-cell line),
MT-6 (HTLV-1$^+$ human T cell lymphoma line)
HHV7

CD4$^+$ T cells
Poxvirus

Epithelial cells.
Vaccinia - broad host range
Small pox - macrophages, epithelial and mucous membranes In one embodiment one uses the entire envelope glycoprotein, but one does not have to. Envelope glycoproteins are typically processed from a single precursor to two proteins. For example, with HIV, the gp160 precursor is processed to form a gp120 and gp41. Similarly, Ebola has a precursor GP which by post-transcriptional modification becomes a GP$_1$ and a GP$_2$. In some instances one can enhance processing by removing the cleavage site, transmembrane domain and/or cytoplasmic tail. Other portions can be deleted also. The key is to retain the cellular binding portion. Typically this is the receptor binding portion(s). Thus, if the virus targets one receptor, only that receptor binding site may be necessary. However, there are instances where co-factors are also used for viral entry and those sites also need to be retained.

In an alternative embodiment, one can use different lentiviral capsids with a pseudotyped envelope. For example, FIV or SHIV [U.S. Pat. No. 5,654,195] a SHIV pseudotyped vector can readily be used in animal models such as monkeys.

The preferred lentivirus is a primate lentivirus [U.S. Pat. No. 5,665,577] or a feline immunodeficiency virus (FIV) [Poeschla, E. M., et al., Nat. Medicine 4:354–357 (1998)] The pol/gag nucleic acid segment(s) and the env nucleic acid segment will when expressed produce an empty lentiviral particle. By making the above-described modifications such as deleting the tat coding region, the MA coding region, or the U3 region of the LTR, the possibility of a reversion to a wild type virus has been reduced to virtually nil.

The lentiviral virion (particle) is expressed by a vector system encoding the necessary viral proteins to produce a virion (viral particle). Preferably, there is at least one vector containing a nucleic acid sequence encoding the lentiviral pol proteins necessary for reverse transcription and integration, operably linked to a promoter. Preferably, the pol proteins are expressed by multiple vectors. There is also a vector containing a nucleic acid sequence encoding the lentiviral gag proteins necessary for forming a viral capsid operably linked to a promoter. Preferably, this gag nucleic acid sequence is on a separate vector than at least some of the pol nucleic acid sequence, still more preferably it is on a separate vector from all the pol nucleic acid sequences that encode pol proteins.

Numerous modifications can be made to the vectors, which are used to create the particles to further minimize the chance of obtaining wild type revertants. These include deletions of the U3 region of the LTR, tat deletions and matrix (MA) deletions.

The gag, pol and env vector(s) do not contain nucleotides from the lentiviral genome that package lentiviral RNA, referred to as the lentiviral packaging sequence. In HIV this region corresponds to the region between the 5' major splice donor and the gag gene initiation codon (nucleotides 301–319).

The vector(s) forming the particle preferably do not contain a nucleic acid sequence from the lentiviral genome that expresses an envelope protein. Preferably, a separate vector that contains a nucleic acid sequence encoding an envelope protein operably linked to a promoter is used. This env vector also does not contain a lentiviral packaging sequence. In one embodiment the env nucleic acid sequence encodes a lentiviral envelope protein.

A desired family of heterologous nucleic acid segments (sometimes referred to as the target molecules) can be inserted into the empty lentiviral particles by use of a plurality of vectors each containing a nucleic acid segment of interest and a lentiviral packaging sequence necessary to package lentiviral RNA into the lentiviral particles (the packaging vector). Preferably, the packaging vector contains a 5' and 3' lentiviral LTR with the desired nucleic acid segment inserted between them. The nucleic acid segment can be an antisense molecule or more preferably, encodes a protein such as an antibody. The packaging vector preferably contains a selectable marker. These are well known in the art and include genes that change the sensitivity of a cell to a stimulus such as a nutrient, an antibiotic, etc. Genes include those for neo puro, tk, multiple drug resistance (MDR), etc. Other genes express proteins that can readily be screened for such as green fluorescent protein (GFP), blue fluorescent protein (BFP), luciferase, LacZ, nerve growth factor receptor (NGFR), etc.

As used herein, the introduction of DNA into a host cell is referred to as transduction, sometimes also known as transfection or infection.

One can set up systems to screen cells automatically for the marker. In this way one can rapidly select transduced cells from non-transformed cells. For example, the resultant particles can be contacted with about one million cells. Even at transduction rates of 10–15% one will obtain 100–150,000 cells. An automatic sorter that screens and selects cells displaying the marker, e.g. GFP, can be used in the present method.

When an inducible promoter is used with the target molecule, minimal selection pressure is exerted on the transformed cells for those cells where the target molecule is "silenced". Thus, identification of cells displaying the marker also identifies cells that can express the target molecule. If an inducible promoter is not used, it is preferable to use a "forced-expression" system where the target molecule is linked to the selectable marker by use of an internal ribosome entry site (IRES) (see Marasco et al., PCT/US96/16531). In this manner, virtually all cells selected on the basis of the marker also contain and can express the target molecule.

IRES sequences are known in the art and include those from encephalomycarditis virus (EMCV) [Ghattas, I. R. et al., Mol. Cell. Biol., 11:5848–5849 (1991)]; BiP protein [Macejak and Sarnow, Nature, 353:91 (1991)]; the Antennapedia gene of Drosophila (exons d and e) [Oh et al., Genes & Development, 6:1643–1653 (1992)]; those in polio virus [Pelletier and Sonenberg, Nature, 334:320–325 (1988); see also Mountford and Smith, TIG, 11: 179–184 (1985)].

Figure 2A:
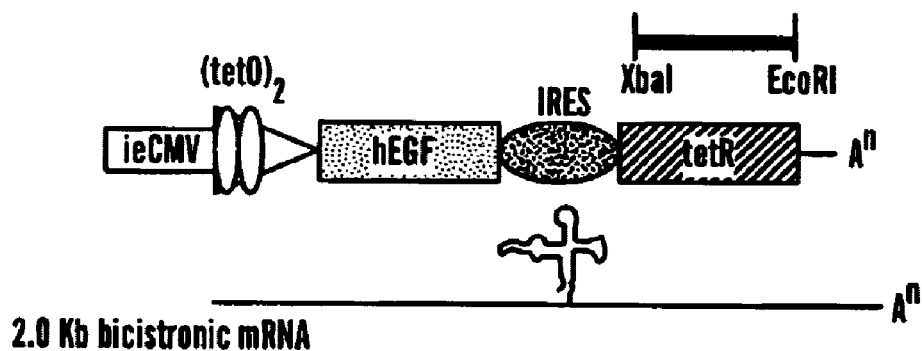
FIGS. 2A and 2B show tetR-mediated repression of transcription initiation.

Preferably, the target molecule is operably linked to an inducible promoter. Such systems allow the careful regulation of gene expression. See Miller, N. and Whelan, J., Human Gene Therapy, 8:803–815 (1997). Such systems include those using the lac repressor from E. coli as a transcription modulator to regulate transcription from lac operator-bearing mammalian cell promoters [Brown, M. et al., Cell, 49:603–612 (1987)], and those using the tetracycline repressor (tetR) [Gossen, M., and Bujard H., Proc. Natl. Acad. Sci. USA 89:5–547–5551 (1992); Yao, F. et al., Human Gene Therapy, 9:1939–1950 (1998); Shockelt. P., et al., Proc. Natl. Acad Sci. USA, 92:6522–6526 (1995)]. Other systems include FK506 dimer, VP16 or p65 using castradiol, RU486, diphenol murislerone or rapamycin [see Miller and Whelan, supra at FIG. 2] such as FK506/rapamycin, RU486/mifepristone. Another system is the ecdysone inducible system. Inducible systems are available from Invitrogen, Clontech and Ariad. Systems using a repressor with the operon are preferred. For example, the Idc repressor from Escherichia coli can function as a transcriptional modulator to regulate transcription from lac operator-bearing mammalian cell promoters [M. Brown et al., Cell, 49:603–612 (1987)] M. Gossen et al. [Proc. Natl. Acad. Sci. USA, 89:5547–5551 (1992)] combined the tetracycline repressor (tetR) with the transcription activator (VP16) to create a tetR-mammalian cell transcriptional activator fusion protein, tTa (tetR-VP16), with the tetO-bearing minimal promoter derived from the human cytomegalovirus (hCMV) major immediate-early promoter to create a tetR-tet operator system to control gene expression in mammalian cells. Recently Yao and colleagues (F. Yao et al., Human Gene Therapy, supra; Ohkawa, J., Human Gene Therapy 11:577–585 (2000)] have demonstrated that the tetracycline repressor (tetR) alone, rather than the tetR-mammalian cell transcription factor fusion derivatives can function as potent trans-modulator to regulate gene expression in mammalian cells when the tetracycline operator is properly positioned downstream of the TATA element of a promoter such as the CMVIE promoter. One particular advantage of this tetracycline inducible switch is that it does not require the use of a tetracycline repressor-mammalian cell transactivator or repressor fusion protein, which in some instances can be toxic to cells [M. Gossen et al., Proc. Natl. Acad. Sci. USA 89:5547–5551 (1992); P. Shockett et al., Proc. Natl. Acad. Sci. USA 92:6522–6526 (1995)], to achieve its regulatable effects. Preferably, the repressor is linked to the target molecule by an IRES sequence. Preferably, the inducible system is a tetR system. More preferably the system has the tetracycline operator downstream of a promoter's TATA element such as with the CMVIE promoter. See FIG. 4.

The effectiveness of some inducible promoters increases over time. In such cases one can enhance the effectiveness of such systems by inserting multiple repressors in tandem, e.g. TetR linked to a TetR by an IRES. Alternatively, one can wait at least 3 days before screening for the desired function. While some silencing may occur, given the large number of cells being used, preferably at least $1 \times 10^4$, more preferably at least $1 \times 10^5$, still more preferably at least $1 \times 10^6$, and even more preferably at least $1 \times 10^7$, the effect of silencing is minimal. One can enhance expression of desired proteins by known means to enhance the effectiveness of this system. For example, using the Woodchuck Hepatitis Virus Post-transcriptional Regulatory Element (WPRE). See Loeb, V. E., et al., Human Gene Therapy 10:2295–2305 (1999); Zufferey, R., et al., J. of Virol. 73:2886–2892 (1999); Donello, J. E., et al., J. of Virol. 72:5085–5092 (1998).

A wide range of nucleic and sequences can be delivered by the present system. One preferred a group of sequences encode antibodies. Antibodies have long been used in biomedical science as in vitro tools for the identification, purification and functional manipulation of target antigens. Antibodies have been exploited in vivo for diagnostic and therapeutic applications as well. Recent advances in antibody engineering have now allowed the gene encoding antibodies to be manipulated so that the antigen binding domain can be expressed intracelluarly. The specific and high-affinity binding properties of antibodies, combined," with the ability to create of large human immunoglobulin libraries and their ability to be stably expressed in precise intracellular locations inside mammalian cells, has provided a powerful new family of molecules for gene therapy applications. These intracellular antibodies are termed "intrabodies" [W. Marasco et al., Gene Therapy. 4:11–15 (1997)]. Preferably, the genes encode a single chain antibody. The molecules preferably contain a tag such as HA so the molecule can be identified later.

Figure 6:
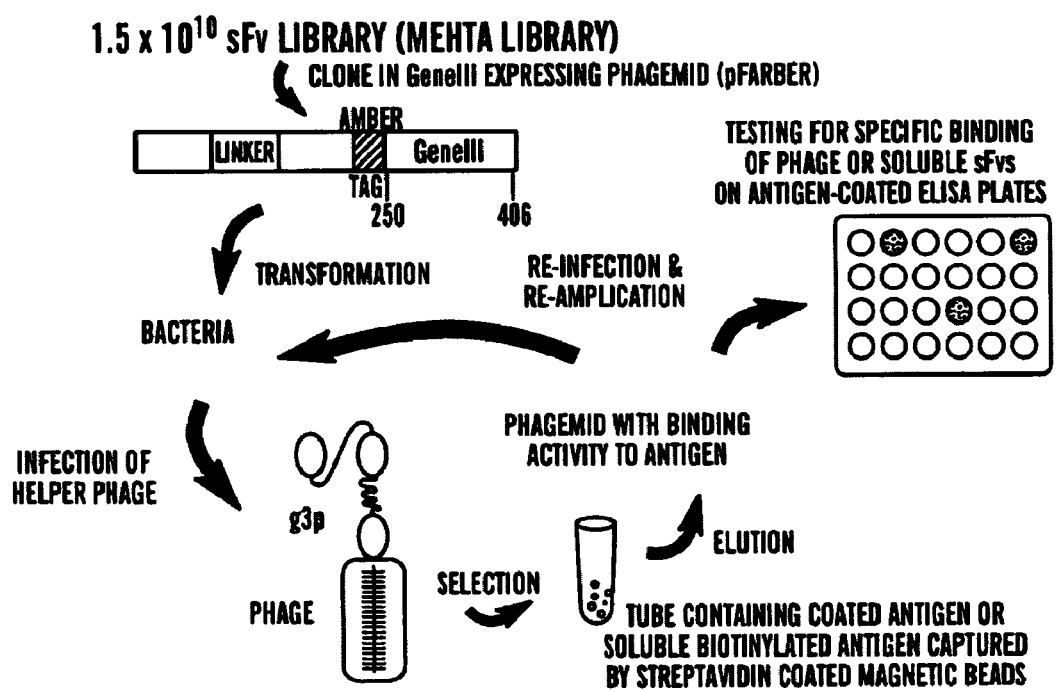
FIG. 6 is a schematic showing how to isolate single-chain antibodies (sFv) by phage display technology.

The antibodies are preferably obtained from a library of antibodies such as a phage display library. FIG. 6 shows a simple method to obtain the antibody and insert it into the packaging vector.

Thereafter the lentiviral vectors are used to transduce a host cell. One can rapidly select the transduced cells by screening for the marker. Thereafter, one can take the transduced cells and grow them under the appropriate conditions or insert those cells e.g. spleen cells or germ cells, into a host animal.

The inducible promoter is turned on and one screens for cells and/or animals displaying a particular phenotype. For example, enhanced expression or lack of expression of a particular receptor, selective killing of abnormal cells, etc. The cells displaying the desired phenotype are selected for and depending upon the phenotype, the selection can be by a high throughput automated screening. For example, beads to select cells displaying a particular receptor. FACS analysis can be used to identify the change in expression of particular receptors. Other systems can readily be identified. Using the tag contained on the molecule, e.g. antibody, one can obtain the molecules. e.g., antibody that resulted in the desired phenotype. In one example, the antibody can then be used to identify the antigen it bound to, if that is desired.

This method permits one to use a multitude of molecules to identify a specific molecule providing the desired function from a large group of molecules without first needing to know the specific identity of any member.

In one embodiment, the vector construct uses an env gene such as VSV-G, in a VSV-G pseudotyped HIV-1 vector system in which the target molecules comprise a very large ($1 \times 10^{10}$ member) human ER-directed sFv intrabody library cloned and expressed under the control of an inducible promoter such as the tetracycline inducible promoter system of Yao, supra. Other env can be used depending upon the host cell chosen. Intrabodies that are targeted, for example, to the lumen of the ER provide a simple and effective mechanism for inhibiting the transport of plasma membrane or secreted proteins to the cell surface; even highly abundant cell-surface receptors have been reduced to undetectable levels using this method. This vector system can be used to identify sFv intrabodies that can cause "phenotypic" knockout resulting in a desired function. For example, killing a malignant cell, but not a corresponding normal cell, elimination of a preselected cell surface molecule, modification of pathobiological process(es), etc. [W. Marasco et al., *Gene Therapy*, 4:11–15 (1997)]. Moreover, since the target molecule, e.g. the sFv intrabodies, are tagged, HA-tagged, discovery and identification of the gene products knocked-out by the sFv intrabody can be readily accomplished through standard laboratory procedures.

Figure 4:
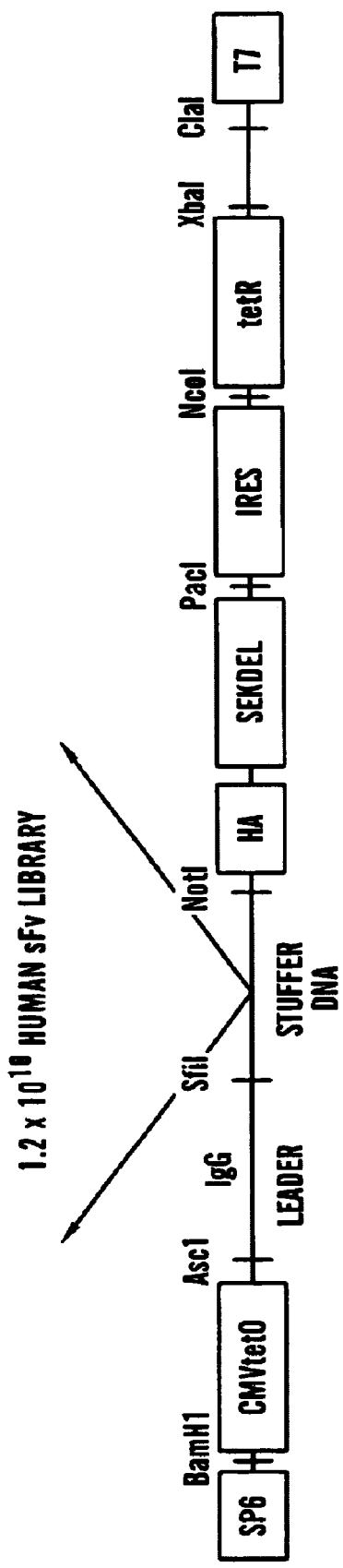
FIG. 4 is a schematic diagram of a cloning vector, pGEM-72f(t) used to transfect the library of target molecules (SEQ ID NO: 3).

Intrabodies that are intended for localization in the ER are preferably equipped with a leader peptide and a C-terminus ER retention signal (the KDEL (SEQ ID NO: 2) amino acid motif—Lys Asp-Glu-Leu SEQ ID NO: 2) [J. Richardson et al., Gene Therapy, 6:635–644 (1998); J. Richardson et al., Virology, 237:209–216 (1997)], although other constructs can readily be made. An intermediate cloning vector allows the sFv library to be cloned directly as sFv cassettes (via for example, identical SfiI/NotI restriction sites) into a vector which contains an immunoglobulin leader sequence, an in frame cloning site for the sFvs, followed by a HA tag sequence and the ER retention sequence SEKDEL (FIG. 4, SEQ ID NO: 3). Electroporation competent TG1 cells can be used to clone the sFv gene cassettes and obtain circa 1×1010 transformants in this intermediate vector. From these transformants, the appropriate fragments, such as BamHI/Xbal fragments, will be isolated, which contain the inducible cassette, e.g., CMVtetO promoter, the ER-directed sFv intrabody library, IRES and tetR. Again electroporation competent TG1 cells are used to clone the BamHI/Xbal fragments into a lentiviral vector such as an inducible system as represented by HIVNtetOIR (FIG. 5) to obtain circa 1×1010 transformants.

HIV-1 vectors expressing for example the ER-directed intrabody library are produced by co-transfection of for instance vectors, pCMVgag-pol, pRev and pVSV-G cDNAs into 293T cells using Superfect (Olagen) [J. Richardson et al., *Gene Therapy*, 6:635–644 (1998)]. Cell culture supernatants are harvested 48–72 hours later. Ultracentrifugation are used to increase the titer of the VSV-G pseudotyped vectors and result in obtaining titers of $10^6$ to $10^8$ infectious particles per ml. The vectors are normalized for reverse transcriptase activity. Transduction efficiencies can be measured on CD4+ SupT cells and 293T cells by FACS analysis of NGFR surface expression 48 hours after transduction. For instance, 293T cells are preferred over COS cells because they are more efficient than COS in giving a higher titer of vectors.

For example, the resulting HIVNtetOIR vectors produced above contain a library of ER-directed sFv intrabodies that have the potential to cause "phenotypic" and/or "functional" knockouts because of intracellular retention/degradation of molecules that translocate through the ER including cell surface and secretary molecules. These vectors can be used to transduce the sFv intrabody library into CD4+ SupT cells to isolate sFv intrabodies that cause phenotypic knockout of specific molecules that are known to be expressed on the surface of these cells. For example, CD4, CXCR4 and MHCI are expressed in high levels on the surface of SupT cells. Other receptors can readily be chosen. These antibodies can also be used to target antigens that are compartments of the cell other than the ER-Golgi apparatus by having the leader sequence deleted. Additionally, a target sequence such as one for the nucleus, mitochondria, etc. can readily be chosen and used in the cassette containing the target molecule.

Thereafter, the host cell can be transduced. For example, SupT cells are optimally transduced and selected for the marker, e.g. NGFR expression. Preferably at least $10^7$ transduced cells are isolated by known means, e.g. beads, affinity chromatography, etc. Cells are treated with the inducer, e.g., 1 µg/ml tetracycline, and allowed to go through two to four additional doublings so that more than one copy of each sFv intrabody gene is present in the pool of stably transduced cells. Approximately $5 \times 10^7$ to $1 \times 10^8$ cell in one to two ml are stained for identification of the desired phenotype, such as with the appropriate anti-CD4, CXCR4 or MHCI Mab followed by FITC-labeled antimouse IgG. The cells are sorted on for example, a MoFlo flow cytometer, which has high throughput capacity (>$5 \times 10^7$ cells/ml/hr). The lowest 10% of FITC labeled cells which will include dead cells, poorly stained cells and phenotypic knockout cells are collected and expanded in tissue culture. This procedure is repeated until populations of cells are recovered which are at least 50% negative for surface expression of the appropriate surface molecule.

Cell surface negative cells from the 50% negative pools mentioned above are subcloned by limiting dilution and used for further biochemical and genetic analysis. Radioimmunoprecipitation experiments with anti-HA Mab are used to co-immunoprecipitate the target molecule. Pulse-chase analysis can be used to determine the half-life of the sFv/target protein complex. Immunofluorescence can be used to determine if the subcellular location of the target molecule has been altered.

The target molecule, such as the sFv genes can be readily recovered by PCR or RT PCR amplification using primers that are located in for example the IgG leader and SEKDEL (SEQ ID NO: 3) regions. The target molecule can be used to identify the ultimate target, i.e., the protein the antibody binds to. These sFv genes are cloned into for example the pSYN bacterial expression plasmid that contains the pelB leader sequence to direct the sFv into the periplasm, SfiI/NotI restriction sites for direct cloning of the sFv, followed by a c myc tag and His6 sequence. Typical yields of sFvs recovered from periplasmic fractions of TG1 strain of *E. coli* that are subsequently purified on IMAC columns range between 160 g to 2 mg per liter from shaker flasks. Thes e sFvs can then be used for direct staining of sFv binding of the cell surface target molecule of interest (using Mab against c myc) or for Western blot analysis of cell extracts. One can also use nanosequencing or GC mass spec to identify a sequence or protein (e.g., a target) where only a small amount of the product is present. See, e.g., Jin, Y., et al., J. of Biol. Chem. 274:28301–28307 (1999) at 28304–305.

The lentiviral virion (particle) is expressed by at least one vector containing a nucleic acid sequence encoding the lentiviral pol and gag proteins necessary for viral protein expression operably linked to a promoter. Preferably, multiple vectors are used. Preferably, the pol sequences encoding pol proteins are on more than one vector. There is also a vector having nucleic acid sequence encoding the lentiviral gag proteins necessary for reverse transcription and integration operably linked to a promoter. Preferably, this gag nucleic acid sequence is on a separate vector than the pol nucleic acid sequence. The use of separate vectors for the various "genes" further reduces the chance of a reversion to wild-type.

In one embodiment, the lentiviral vector is modified so that the gag sequence does not express a functional MA, protein, i.e. it is MA. This can be accomplished by inactivating the "gene" encoding the MA by additions, substitutions or deletions of the MA coding region. Since the MA is part of the gag gene and as expressed, is processed from the precursor protein, when referring to a MA gene (or coding region), we are only referring to that portion of the entire gag gene that encodes the MA subunit. Preferably, the inactivation is accomplished by deletion. Preferably, at least 25% of the MA coding region is deleted, more preferably, at least 50% is deleted, still more preferably, at least 60%, even more preferably at least 75%, still more preferably, at least 90%, yet more preferably at least 95% and most preferably the entire coding region is deleted.

The MA has a myristylation anchor and that myristylation anchor (sequence) is required. Preferably, the myristylation sequence is a heterologous (i.e., non-lentiviral) sequence. Src, MARCKS (myristolylated alanine-rich C kinase substrate), ARF (ADP-ribosylation factor), recovering and related EF-hand calcium-binding proteins (visinin neurocalcium and others), and non-lentiviral gag proteins (e.g., Moloney murine leukemia virus. Mason-Pfizer monkey virus).

The MA-deleted viruses consistently exhibit an increased ability to release extracellular virus particles, indicating that there is no requirement for the globular domain of MA for stable membrane association. Surprisingly, deleting the globular head of MA, which harbors the putative MA nuclear localization signal (NLS), also permits the early steps of the lentiviruses replication cycle in macrophages.

In one embodiment the env nucleic acid sequence encodes a lentiviral envelope protein. When using a MA- gag vector, it is preferred that the env sequence is altered from the wild type sequence so that it encodes a truncated cytoplasmic tail. Preferably, 50% of the cytoplasmic tail is missing. More preferably, at least 75% is deleted still more preferably at least 90% is deleted, even more preferably, at least 95% is deleted. Most preferably, the entire cytoplasmic tail is deleted in such an embodiment.

In another embodiment the lentiviral vector is another form of self-inactivating (SIN) vector as a result of a deletion in the 3' long terminal repeat region (LTR). Preferably, the vector contains a deletion within the viral promoter. The LTR of lentiviruses such as the HIV LTR contains a viral promoter. Although this promoter is relatively inefficient, when transactivated by e.g. tat, the promoter is efficient. However, the presence of the viral promoter can interfere with heterologous promoters operably linked to a transgene. To minimize such interference and better regulate the expression of transgenes, the lentiviral promoter is preferably deleted.

Preferably, the vector contains a deletion within the viral promoter. The viral promoter is in the U3 region of the 3' LTR. A preferred deletion is one that is 120 base pairs between ScaI and PvuI sites, e.g. corresponding to nucleotides 9398–9518 of HIV-1 HXBC encompassing the essential core elements of the HIV-1 LTR promoter (TATA box, SP1 and NF—Pb binding sites). The further 5' you go downstream the more dramatic the "SIN" effect. Indeed, deletions of up to 400 base pairs have proven effective. Zuffrerey, R., et al., J. of Virol 72:9873–9880 (1998). After reverse transcription, the deletion is transferred to the 5' LTR, yielding a vector/provirus that is incapable of synthesizing vector transcripts from the 5' LTR in the next round of replication. Thus, the vector of the present invention contains no mechanism by which the virus can replicate as it cannot express the viral proteins.

In another embodiment the vector is a tat deleted vector. This can be accomplished by inactivating at least the first exon of tat by known techniques such as deleting it or introducing a stop codon. Alternatively, one can extend the U3 LTR deletion into the R region to remove the TAR element. The tat deleted vectors result in high titer of virus.

Variations can be made where the lentiviral vector has multiple modifications as compared to a wildtype lentivirus. For example, with HIV being nef-, rev-, vif- and vpr-. In addition one can have MA-gag, 3' and 5'U3 deleted LTR and variations thereof.

By using these techniques a number of safety redundancies are introduced into the vectors.

In a more preferred embodiment, the env sequence encodes an envelope protein from a different virus than the lentiviral gag and pol genes. The resultant particle is referred to as a pseudotyped particle. By appropriate selection of the envelope protein one can transform virtually any cell. Preferably envelopes are influenza virus, VSV, filoviruses such as Ebola, more preferably VSV-G or Ebola.

As discussed above, the envelope protein chosen can effect the host range. For example, a VSV-G pseudotyped particle will infect a wide range of cells. Whereas Ebola pseudotyped particles or HTLV-pseudotyped particles have a limited host range.

While env glycoproteins are dispensable for particle production per se, their ion is required for the formation of infectious virions.

The vector system can be used to package a wide range of desired nucleotide preferably a RNA segment, into an empty lentiviral particle because of the large of lentiviruses. In addition, the use of promoters and enhancers can also significantly length of an insert. Preferably, the system is used with groups containing multiple molecules displaying diversity such as genetic diversity. Accordingly, the system of the present invention provides a significant advantage over currently available vectors by allowing for inserts that can contain a number of promoters and genes and that can be used to transfect resting cells as well as dividing cells.

The vector(s) is prepared so that none of the nucleotide segments used will contain a functional packaging site containing sequence. (This sequence is referred to as the packaging sequence.)

The vector(s) do not contain nucleotides from the lentiviral genome that package lentiviral RNA, referred to as the lentiviral packaging sequence. In HIV this region corresponds to the region between the 5' major splice donor and the gag gene initiation codon (e.g., nucleotides 301–319 in HXB2). Preferably, these vectors also do not have lentiviral LTRs such as the HIV LTR. The env, gag, and pol genes are operably linked to a heterologous promoter.

The packaging sequence can be excluded from the vector(s) by any of a variety of techniques well known to the person of ordinary skill in the art. For example, one can simply delete the entire sequence. Alternatively, one can delete a sufficient portion of a sequence to render it incapable of packaging. An alternative strategy is to insert nucleotides into such a site to render it non-functional. Most preferably, one will delete the site entirely to prevent homologous recombination.

Accordingly, the lentiviral vectors can express the desired viral proteins, but because the packaging site has been removed and the lentiviral LTRs are not operational, their mRNA will not be effectively packaged into the lentiviral particles, and the recombinant virus will not be able to replicate and infect other cells.

The lentiviral vectors can also contain sequences encoding desired lentiviral regulatory proteins such as Tat, Rev, etc. However, in a number of embodiments it is preferable not to contain such regulatory genes. If RRE and CAR sequences are included in the gene, the inclusion of sequence encoding RREV is necessary in this, unless the virus is expressed in the cytoplasm. Alternatively, you can use constitutive transport elements (CTE) in place of RRE to make the vectors REV independent. Also, there is less sequence homology. Srinivasakumar, S., et al., *J. of Virol.*, 73:9589–9598 (1999); Srinivasakumar, et al., *J. of Virol.*, 71:5841–5848 (1997). These regulatory sequences can be on the other lentiviral vectors (e.g., gag vector, pol vector, gag-pol vector or env vector), or on their own lentiviral vector.

A desired heterologous nucleic acid segment can be encapsulated within the empty lentiviral particle by using a vector containing a nucleic acid segment of interest and a lentiviral packaging sequence necessary to package lentiviral RNA into the lentiviral particles at the time the lentiviral vectors are used. Preferably, the vector contains a 5' and 3' lentiviral LTR with the desired nucleic acid segment inserted between them. The nucleic acid segment preferably encodes a protein.

An origin of DNA replication (ori) which is recognized by the viral replication proteins and enzymes may also be present. This vector permits packaging of desired nucleotide inserts in the pseudotyped particles. This vector is sometimes referred to as the packaging vector. This packaging vector is used to package any group of desired heterologous nucleic acid sequence, preferably a RNA sequence, into the particle. Preferably, the packaging vector contains (a) a promoter sequence operably linked to at least one heterologous nucleic acid sequence and (b) at least one sequence sufficient to permit transcription and processing of mRNA, the translation of which results in an expressed protein. Preferably, the processing sequence is a polyadenylation sequence. Preferably the promoter is part of an inducible system. Still more preferably, this vector contains an intervening sequence following the promoter sequence. Preferably the sequences containing the promoter, target molecule, and optionally a repressor sequence also contains a tag such as HA to permit ready identification of the target molecule. This grouping of elements is sometimes also referred to as the cassette. For example, the heterologous sequence can encode any desired protein, preferably a therapeutic protein or an antibody. It can also encode antisense DNA, RNA or a desired immunogen, such as an antigenic protein. It can encode specific peptide sequence that will generate an immunogenic reaction. Such a peptide sequence is typically at least about 6 amino acids in length.

The heterologous nucleotide sequence can encode a wide variety of proteins such as a therapeutic protein, i.e., one that compensates for an inherited or acquired deficiency. Examples of therapeutic proteins include neurotransmitter biosynthetic enzymes, e.g., tyrosine hydroxylase for the treatment of Parkinson's disease; neurotrophic factors including neutrophins, e.g., nerve growth factor for the treatment of Alzheimer's disease, one can also use nerve growth factor receptor and the trk receptor; hypoxanthine-guanine porphoribosyl transferase (HGPRT) for the treatment of Lesch Nyhan disease; β-hexosaminadase a chain for the treatment of Tay Sachs disease; insulin for the treatment of diabetes; angiogenic proteins such as VEGF, bFGF for the treatment of ischemic tissues, circulatory problems, etc., antianglogenic proteins for treating malignant cells such as platelet factor IV, endostaten, etc. Receptors can also be delivered, e.g. the nerve growth factor receptor, the trk receptor, etc. Because the insert can be large, it is possible to encode a series of different proteins. For example, one can encode a series of proteins that form a receptor-ligand complex.

Other proteins include, for example, signal transduction enzymes, e.g., protein kinase c; transcription factors, e.g., c-fos, NF-PB; oncogenes, e.g., erbB, erbB-2/neu, ras; neurotransmitter receptors, e.g., glutamate receptor, dopamine receptor, etc.

One preferred group of proteins that are encoded are angiogenic proteins. As used herein the term "angiogenic protein" means any protein, polypeptide, mutein or portion that is capable of, directly or indirectly, inducing blood vessel growth. Such proteins include, for example, acidic and basic fibroblast growth factors (aFGF and bFGF), vascular endothelial growth factor (VEGF) including VEGF-1 and 2,epidermal growth factor (EGF), transforming growth factor I and θ (TGF-I and TGF-θ), platelet-derived endothelial growth factor (PD-ECGF), platelet-derived growth factor (PDGF), tumor necrosis factor I (TNF-I), hepatocyte growth factor (HFG), insulin like growth factor (IGF), eryhropoietin, colony stimulating factor (CSF), macrophage-CSF (M-CSF), granulocyte/macrophage CSF (GM-CSF), angiopoetin-1 (Ang1) and nitric oxidesynthase (NOS). See, Klagsbrun, et al., *Annu. Rev. Physiol.*, 53:217–239 (1991); Folkman, et al., *J. Biol. Chem.*, 267: 10931–10934 (1992) and Symes, et al., *Current Opinion in Lipidology*, 5:305–312 (1994). Muteins or fragments of a mitogen may be used as long as they induce or promote blood vessel growth.

VEGF is a preferred angiogenic protein. VEGF-1 exists in several different isoforms that are produced by alternative splicing from a single gene containing eight exons (Tischer, et al., *J. Biol. Chem.*, 806, 11947–11954 (1991), Ferrara, *Trends Cardio. Med.*, 3, 224–250 (1993), Polterak, et al., *J. Biol. Chem.*, 272, 7151–7158 (1997)). Human VEGF isoforms consists of monomers of 121 (U.S. Pat. No. 5,219, 739), 145, 165 (U.S. Pat. No. 5,332,671), 189 (U.S. Pat. No. 5,240,848) and 206 amino acids, each capable of making an active homodimer (Houck, et al., *Mol. Endocrinol.*, 8, 1806–1814 (1991)). Other forms of VEGF include VEGF-B and VEGF-C (Joukou, et al., *J. of Cell. Phys.* 173:211–215 (1997), VEGF-2 (WO 96/39515), and VEGF-3 (WO 96/39421).

Another preferred group of encoded proteins are antibodies. Included are dAbs, single chain antibodies, Fabs. Single chain antibodies are preferred. Libraries of antibodies are known and can be used in the present invention. For example, using a phage display library both generalized and specialized libraries can be used. A specialized library would be one where the member antibodies are generated to a specific group of antigens, e.g. a specific tumor. The diversity of the members of a specialized library is less than that of a generalized library.

The heterologous nucleotide sequence can also encode antisense molecules (DNA or RNA). These molecules can be used to regulate gene expression associated with a particular disease. The antisense molecules are obtained from a nucleotide sequence by reversing the orientation of the coding region with regard to the promoter. Thus, the antisense RNA is complementary to the corresponding mRNA. For review of antisense science see Green, et al., *Ann. Rev. Biochem.* 55: 569–597 (1986), which is herein incorporated by reference. The antisense sequence can contain modified sugar phosphate backbones to increase stability and make them less sensitive to RNA sensitivity. Examples of the modifications are described by Rossi, et al., *Pharmacol. Ther.* 50(2):245–354 (1991). Another class of molecule includes ribozymes. Ribozymes and antisense molecules that engage in, as well as those that do not show transplicing can be used.

The heterologous nucleotide sequence is preferably operably linked to a promoter sequence capable of directing transcription of the sequence in a desired target cell. Lentiviruses such as the primate lentiviruses contain the Tat regulatory protein. This protein will transactivate a protein operably linked to a TAR element. The TAR element is present in the 5' LTR of the primate lentivirus. Thus, the expression of heterologous protein can be enhanced by transactivation. The LTR also contains a promoter. However, that promoter in the absence of transactivation is relatively ineffective. Thus, the use of other promoters and enhancers is typically preferred. The promoter can be a promoter such as the SV40, CMV, HSV-1 IE, IE 4/5 or RSV (Rous sarcoma virus) promoters. Others include Srα-promoter (a very strong hybrid promoter composed of the SV40 early promoter fused to the R/U5 sequences from the HTLV-I LTR), tetracycline-regulatable promoters, tissue-specific promoters (e.g., alpha-fetoprotein promoter; and rhodopsin promoter for photoreceptor-targeted expression). Other promoters capable of directing transcription of the heterologous sequence in a specific target cell can also be used to more specifically direct expression of the heterologous gene to a desired target (host) cell. Indeed, one can link the inducible promoter construct with a tissue specific promoter. For example, if the target cell is a neuronal cell, a promoter such as the neuron specific enolase promoter [Forss-Petter. et al., *J. Neurosci. Res.* 16: 141–56 (1986)] can be used. The rat tyrosine hydroxylase (TH) promoter can support cell type specific expression in the midbrain [S. Song et al., *J. Neurochem:* 68: 1792–803 (1997)]. Furthermore. the use of inducible promoters or other inducible regulatory sequences, which are well known in the art, in some embodiments are preferred. For example, the tetR-tetO system. As discussed the promoter in the LTR can interfere with the other promoter. Thus, in certain embodiments it is preferable to inactivate the viral LTR promoter.

In order to minimize the possibility of a recombination event between the packaging vector that transfers the desired heterologous gene(s) and the lentiviral vector generating a wild type lentivirus, it is desirable that the packaging vector has a minimal degree of homology with the nucleotide segments encoding the particle vector. Preferably, one would use different promoters in these different vectors. These goals can be accomplished by a variety of means known in the art based upon the present disclosure. For example, in order to minimize any chance of recombination, it is preferable to use multiple vectors. Additionally, it is preferable to reduce the chance of homologous recombination by minimizing sequence overlap. For example, one can delete unnecessary lentiviral sequences. Alternatively or additionally, one can use known techniques to change the nucleotide sequence of the vectors. One method of accomplishing this is referred to as nucleotide, e.g., DNA, shuffling. One changes nucleotides in codons, e.g., the third base of each codon within the lentiviral constructs of one vector. Thus, the same coding sequence in a second vector now differs and will not be subject to homologous recombination. Changes in the codons of the various vectors can be made to optimize nucleotide differences.

Alternatively or in combination with the above approach of reducing homology, one can alter the sequence of a gene from the lentivirus segment so that it does not encode a functional protein. As used herein "functional" means a protein having wild-type activity.

Depending upon the particular purpose for the particles one can use known techniques to alter the lentivirus segment to inactivate genes that encode proteins present in the particle which cause certain effects. For example, inactivating those proteins that enhance replication, e.g., rev and/or tat. Vpu affects infectivity. Nef also affects the virus. It has been reported that nef appears to be required for efficient replication in vivo.

Cells can be transfected by the vectors to prepare the viral particle. One can prepare the vectors in vitro, one would then harvest the particles, purify them and inject them by means well known in the art. More preferably one would purify the particles, and then use those to infect the desired cells.

One can create producer cell lines expressing virions and transform such cells with the packaging vector. The producer cell lines or any cell can be transformed by standard techniques. One preferred method is to use an inactivated adenovirus vector linked to the packaging vector by a condensing polycation such as polylysine or polyethylanimine (PEI) [see Baker, A. et al., *Nucleic Acids Res.*, 25(10):1950–1956 (1997); Baker, A. et al., *Gene Ther.*, 4(8):773–782 (1997); Scaria, A. et al., *Gene Ther.*, 2:295–298 (1995)]. The use of PEI is a condensing polycation is preferred.

As used herein, the packaging vector refers to the vector that contains the heterologous gene to be transferred under the control of a promoter (e.g., internal tissue-specific or inducible) flanked by lentiviral LTRs, and the packaging and leader sequences necessary for encapsidation (i.e., packaging). This vector is sometimes referred to in the literature as transfer vector and it is the constructs encoding the proteins and enzymes required for encapsidation that are referred to as the packaging construct.

The vectors express proteins and mRNA which assemble into particles and hence can be used to express large amounts of viral particles. This requires transfecting a cell with the particle vector system described herein, the packaging vector, and culturing the cell line under conditions and time sufficient to express the viral proteins which then form the particles. Thereafter, the particles can be purified by known techniques with care taken to insure that the structure of the particle is not destroyed. The particles can be used in a variety of areas. For example, they can be used to generate a desired immune reaction to transform a cell with a heterologous nucleic acid sequence and/or to deliver a nucleic acid sequence to a desired host cell.

One can prepare transient or stable cell lines that express the lentiviral particles by standard techniques based upon the present teaching.

Thereafter, if stable cell lines are desired, one can screen for those cells that have been stably transfected by standard technique.

Such stable producer cell lines are a preferred source for obtaining packaged particles.

The particles of the present invention can be used to deliver heterologous DNA to a target cell. The target cell may be in vivo, in vitro or ex vivo. The target cell can be a dividing or preferably a quiescent cell. Quiescent cells include nonmitotic or postmitotic cells. The preferred nonmitotic cell is a macrophage. The target cells also include cells of the nervous system, e.g., neural or neuronal cells. Preferred quiescent or slowly dividing target cells include glia cells, myocytes, hepatocytes, pneumocytes, retinal cells, and hematopoietic stem cells. Pancreatic islet cell are also a preferred target.

In the present method the use of in vitro cells in presently preferred. However, there are instances where in vivo or ex vivo administration is desirable.

Introduction of the viral particle carrying the heterologous gene to be delivered to a target cell may be effected by any method known to those of skill in the art. For example, with in vivo administration, the following techniques are preferred. Catheters, injection, scarification, etc. For example, stereotaxic injection can be used to direct the viral particles to a desired location in the brain. Stereotaxic surgery is performed using standard neurosurgical procedures [Pellegrino and Clapp, *Physiol. Behav.* 7: 863–8 (1971)]. Additionally, the particles can be delivered by intracerebroventricular ("icv") infusion using a minipump infusion system, such as a SynchroMed Infusion System. A recent method based on bulk flow, termed convection, has also proven effective at delivering large molecules to extended areas of the brain and may be useful in delivering the viral particle to the target cell [R. Bobo et al., *Proc. Natl. Acad Sci. USA* 91: 2076–80 (1994); P. Morrison et al., *Am. J. Physiol.* 266: R292–305 (1994)]. Other methods can be used including catheters, intravenous, parenteral, intraperitoneal and subcutaneous injection, oral or other known routes of administration.

In some instances one would use these vectors to transform host cells in vivo to look for effects of specific genes in a living system. One would inject a sufficient amount of the separate vectors or preferably the packaged viral particles to obtain a serum concentration in the tissue containing the target cell of the therapeutic protein ranging between about 1 pg/ml to 20 μg/ml. More preferably between about 0.1 μg/ml to 10 μg/ml. Still more preferably, between about 0.5 μg/ml to 10 μg/ml. For example, by expressing a specific protein or alternatively, by blocking the function of a protein such as by expressing an antibody to a specific sequence intracellularly.

For example, solid dose forms that can be used for oral administration include capsules, tablets, pills, powders and granules. In such solid dose forms, the active ingredient, i.e., empty virus particle, is mixed with at least one inert carrier such as sucrose, lactose or starch. Such dose forms can also comprise additional substances other than inert diluents. e.g., lubricating agents, such as magnesium stearate. Furthermore, the dose forms in the case of capsules, tablets and pills may also comprise buffering agents. The tablets, capsules and pills can also contain time-release coatings to release the particles over a predetermined time period.

For parenteral administration, one typically includes sterile aqueous or nonaqueous solutions, suspensions or emulsions in association with a pharmaceutically acceptable parenteral vehicle. Examples of non-aqueous solvents or vehicles are propylene glycol, polyethylene glycol, vegetable oils such as olive oil and corn oil, gelatin and injectable organic esters, such as ethyl oleate. These dose forms may also contain adjuvants such as preserving, wetting, emulsifying and dispersing agents. They may be sterilized by, for example, filtration through a bacterial-retaining filter, by incorporating sterilizing agents into the composition, by irradiating the compositions, etc, so long as care is taken not to inactivate the virus particle. They can also be manufactured in a medium of sterile water or some other sterile injectable medium before use. Further examples of these vehicles include saline, Ringer's solution, dextrose solution and 5% human serum albumin. Liposomes may also be used as carriers. Additives, such as substances that enhance isotonicity and chemical stability, e.g., buffers and preservatives, may also be used.

The preferred range of active ingredient in such vehicles is in concentrations of about 1 mg/ml to about 10 mg/mil. More preferably, about 3 mg/ml to about 10 mg/ml.

EXAMPLES

Construction of a Single-Plasmid Tetracycline-Inducible System

Basic One-Plasmid System

Our single inducible cassette (outlined in FIG. 1A) was constructed by three piece ligation of a internal ribosomal entry site (IRES) from the encephalomyocarditis virus (EMCV) and the tetR fragment removed from pcDNA3tetR into a NotI/ClaI sites of pCMVtetOhEGF [F. Yao et al., *Human Gene Ther.* 9: 1939–1950 (1998)]. The plasmid pCMVtetOhEGF, used as the parental vector for all our constructs contains the human epidermal growth factor (hEGF) gene driven by a chimeric promoter composed of ~650 bp of the immediate early enhancer, cytomegalovirus promoter (ieCMV) and two tandem repeats of the tetracycline operator (tetO) positioned 10 bp downstream of the TATA box. A NotI-NheI fragment encoding the IRES sequence was removed from a previously described vector, pCMV-Fab 105/21H previously prepared by R. Levin et al., *Mol. Med.* 3: 96–110 (1997). A subcloning step, using the intermediate pGem7Zf(+) vector (Promega, Madison, Wis.), was required to clone the XbaI-EcoRI tetR-containing fragment from pcDNA3tetR allowing the introduction of the flanking restriction sites (NheI-ClaI) necessary for the final cloning step as well as the insertion of a Kozak sequence preceding the first ATG [M. Kozak, *J. Mol. Biol.* 196: 947–950 (1987)]. Previous to this step, pGEM7Zf(+) vector was modified by incorporating a synthetic linker containing a HindIII-NheI-Kozak(CCACC)-ATG-XbaI-EcoRI-Stop (TATTAA)-SpeI-ClaI-SphI recognition sites. A pair of oligonucleotides carrying the corresponding sequence was synthesized and equivalent amounts of each (10 μg) were hybridized prior to the final ligation into the HindIII-SphI sites of pGEM7Zf(+) vector. The resulting 0.65 Kb NheI-ClaI-tetR fragment was inserted downstream of the IRES sequence and prior to the polyadenylation site of the pCMVtetOEGF vector. This position allows cap-independent translation of tetR from the single mRNA transcript. The final three piece ligation step was performed using a DNA ligation kit from Takara and according to manufacturer procedures. Similarly, a pCMVhEGF plasmid lacking the tetO was modified to incorporate the IRES sequence and the tetR gene for its use as non-regulatable control plasmid.

Introduction of a Nuclear Localization Signal

A three tandem repeat sequence corresponding to the nuclear localization signal (NLS) from simian virus large T-antigen (GATCCAAAAAAGAAGAGAAAGGTA SEQ ID NO: 1) was incorporated at the 3' end of tetR preceding the stop. A pair of complementary oligonucleotides containing the nls sequence were synthetically prepared and, after hybridization, cloned in frame between the EcoRI and SpeI sites of pGEM7Zf(+)-tetR. Then, constructs previously described were modified by replacing the tetR gene for the tetR.NLS fragment.

Replacement of the hEGF Reporter Gene by eGFP Gene

The BamHIII/NotI fragment containing the hEGF gene was excised from the basic inducible system and replaced by the enhanced green fluorescent protein (eGFP) gene. The 700 bp fragment encoding eGFP was removed from peGFP.IRES.neo vector (Clontech, Palo Alto, Calif.) and directly ligated into the parental constructs.

The final plasmids were purified using the Endotoxin-free Maxi Kit from Qiagen Inc. (Valencia, Calif.).

In Vitro Functionality of Our Single-Plasmid System Versus the Original Two Component Inducible System.

Cell Culture and Transfections

African green monkey kidney cells, Vero. COS-1 and COS-7 cell lines and human kidney 293-T cells were grown and maintained in Dulbecco's modified Eagle's medium (D-MEM) (GIBCO-BRL, Grand Island, N.Y.) supplemented with 10% fetal bovine serum (Tissue Culture Biologicals, Tulare, Calif.) and antibiotics. D-MEM media containing 10% of the Tet System approved fetal bovine serum (Clontech, Palo Alto, Calif.) was used for functional testing of our inducible system.

The day before transfection, cells were subcultured into six-well plates (Becton Dickinson, Franklin Lakes, N.J.) at densities of $2 \times 10^5$ cells/well. Transient transfection assays were performed using the Superfect reagent (Qiagen, Valencia, Calif.) as described by the manufacturer. DNA complexes were prepared using 2.5 µg of plasmid DNA and Superfect reagent at a 1:2 ratio of DNA to condensing agent, followed by incubation at room temperature for 10 min and finally, addition of the complexes to the cells. Comparison with the 2 plasmid system was carried out using 0.5 µg of pCMVtetOhEGF or pCMVhEGF. in each case alone or in combination with 2 µg of pcDNA3tetR or empty vector DNA, pcDNA3.1(–). After 18 hr incubation at 37° C. in a humidified atmosphere of 5% $CO_2$, cells were washed with PBS and refed with fresh media in the presence or absence of tetracycline (1 µg/ml). Reporter gene expression was measured as a function of time after transduction as we detailed in another section.

Evaluation of Reporter Gene Expression

Expression of hEGF in cultured media was performed by the ELISA technique. Briefly, 96 well plates were coated with an anti-hEGF monoclonal antibody (MAB236; R&D Systems, Minneapolis, Minn.) (100 ng/well) at room temperature (RT) for 5 hr and then blocked using 3% non-fat milk in phosphate saline buffer (PBS). Samples, extracellular medium and recombinant HEGF standards prepared in a two-fold dilution series ranging from 9.7–5,000 pg/ml (234-EG; R&D Systems) were incubated at 4° C. overnight. A secondary polyclonal antibody specific to HEGF (sc275; Santa Cruz Biotechnologies. Santa Cruz. Calif.), was then added (100 ng/well) and incubated for 2 hr at RT. The horseradish peroxidase (HRP)-conjugated goat anti-rabbit polyclonal antibody (sc2004; Santa Cruz) was the tertiary antibody (3.33 ng/well). Finally, the peroxidase assay was performed (Bio-Rad, Hercules, Calif.), according to manufacturer's procedures and the reactions analyzed on a microplate reader (Molecular Devices, Sunnyvale, Calif.).

Production of the green fluorescent protein from constructs bearing the eGFP gene was detected by FACS analysis and histochemistry.

RNA Extraction and Northern Blot Analysis

Total cytoplasmic RNA was extracted from transfected cells using the TRIzol Reagent (GIBCO-BRL) and according manufacturer's procedures. RNA (20 µg) was separated on 1.2% formaldehyde/agarose gels and transferred to nylon Hybond-N filter membranes (Amersham, Arlington Heights, Ill.) by pressure blotting. Blots were probed with a XbaI-EcoRI tetR DNA fragment (25 ng) labeled using the Megaprime DNA labeling system (Amershan) and $[^{32}P]$-dCTP (NEN, Boston, Mass.). Overnight hybridization was performed using $4 \times 10^7$ cpm of labeled probe in a solution containing 0.5%[w/v] SDS. 5× Denhardt's solution [0.1% BSA, 0.1% Ficoll, 0.1% PVP] and 5×SSPE [0.9M NaCl, 50 mM sodium phosphate. 5 mM EDTA, pH7.7] at 42° C. Blots were washed at a final stringency of 0.1% SDS, 0.1% SSPE at 60° C. and then visualized by autoradiography after exposure at –80° C.

Immunolocalization of tetR in Transfected Cells

Vero cells ($5 \times 10^4$/well) were plated the day before transfection on chamber glass slides. Transfection of the constructs was performed as described above. Forty-eight hours after treatment (plus or minus 1 µg/ml tet), cells were fixed with 4% formaldehyde in PBS for 20 min at RT. Upon fixation, cells were permeabilized with 0.2% Triton X-100 for 5 min at RT and blocked with 10% normal goat serum, 5% BSA in PBS for 30 min. A monoclonal antibody raised against tetR (Clontech) was added in a 1:100 dilution and incubated for 1–2 hrs. A goat anti-mouse IgG coupled to FITC (Sigma. St. Louis, Mo.) or alternatively labeled with PE (Boeheringer Mannheim) at 1:250 dilution was added to the cells and incubation continued for an hour. After washing with PBS, coverslips were mounted in Sigma medium and examined under the UV light using a fluorescence microscope (Nikon Diaphot 300) with FITC and Rhodamine exchangeable filters. Images recorded in a spot cooled color digital camera were analyzed using the Oncor Image software and printed from Adobe Photoshop, V3.0 for Macintosh.

Preparation and Evaluation of HIV-1-Based Vectors

The vectors used are based on the HIV-1 proviral clone HXB2 (FIG. 1). A more detailed description of the basics for our viral vector construction has been previously reported by Richardson et al., *Gene Ther.*, 5:635–644 (1998).

The original multiple attenuated vector (with deletions in the nef, rev, vif and vpr genes, HVPΔEB) was modified to silence transcriptional activation from the viral promoter region which can otherwise cause interference of transgene expression when using internal promoters (promoter interference). The resulting self-inactivated (SIN) transfer vector or HVPΔEBΔLTR was generated by a simple ScaI/partial PvuII digestion and insertion of a PacI linker, eliminating therefore a 120 bp fragment (nucleotides 9398–9518) encompassing the TATA box, SP1 and NF—κB sites on the 3'LTR. The sequence of the modified U3 region in the transfer plasmid was confirmed by DNA sequencing.

A novel improved version of the original vector was generated by a 2.5 Kb deletion (nucleotides 830–2096 and 5743–7041) into the remaining gag region and the first exon of the tat and rev genes (NVPΔEBΔtat). This fragment was removed by ClaII/ClaI digestion and consequent re-ligation, resulting in a tat-vector.

To determine the transduction efficiency of the three developed vectors, the enhanced green fluorescent protein (eGFP) either under control of the CMV promoter or in absence of any internal promoter was introduced into the transfer vectors. A synthetic linker containing a BamHI-MluI-NotI-XbaI-XhoI sites was inserted into the plasmid vectors to incorporate the suitable cloning sites and then the MluI-NotI CMV EGFP (Clontech, Palo Alto, Calif.) or the BamHI-NotI EGFP fragments were moved into the vectors.

Viral Vector Packaging and Transduction

The pseudotyped HIV-vector particles were produced in COS-1 cells (~1.5×10$^6$ cells/10 mm dish) by transient co-transfection of the transfer vector (5 µg), packaging plasmid (2.5 µg). VSV-G-(1 µg) and rev-expressor (1 µg) plasmids using Superfect reagent (Qiagen) according to manufacturer's instructions. Medium was replaced after 24 hours and virus was harvested 36–48 hours later. The conditioned media was screened for reverse transcriptase activity and 1 ml was used to transduce 1×10$^6$ Hela cells. Transduction efficiency was determined by fluorescent-activated cell sorting (FACS) analysis.

Construction of an Inducible HIV-1 -Based Vector

Replication-deficient VSV-G pseudotyped HIV-1 vectors were generated by transient cotransfection of 293T human kidney cells using three plasmid combination. They consist of a helper construct encoding for the proteins and enzymes necessary for lentiviral production, an envelope-expressor and the transfer vector.

The transfer vector plasmid is devoid of most of the gag-pol and envelope genes but maintains the cis-acting elements necessary for encapsidation, reverse transcription and integration. The pHlibCMVeGFP (wild-type) vector contains a 3.1 Kb deletion into the gag-pol region and two deletions into the env gene region (1.5 and 0.55 Kb) that allows insertion of a foreign gene as well as makes the virus non-replicative. To study the ability of the lentiviral vectors to infect and provide efficient gene expression we have used the enhanced green fluorescent protein (eGFP) gene as a marker gene. hEGF or any other marker could be used instead. Vectors containing the eGFP gene under the control of either the heterologous immediate early CMV promoter or the viral 5' LTR were prepared by standard techniques.

Improvement in vector biosafety was achieved by constructing a self-inactivated vector (SIN vector) by introducing a 120 bp deletion in the 3'LTR region (9398–9518 bp) of the wild type vector. During reverse transcription, the missing DNA fragment is transferred to the 5' LTR region resulting in a deletion of the TATA box. SP1 and NF-kB cis-acting elements that will consequently lead to viral promoter attenuation in the resulting proviral DNA.

We also generated a tat-independent vector by site directed mutagenesis. A three base mutation within the first two codons of the first exon of the tat gene was introduced. resulting in a two amino acid substitution (the first aa, Met to Ile and the second. Glu to a Stop signal).

Two other plasmids required to build an HIV-1 based vector are the packaging construct. pCMV R8.2, and an envelope-expressor plasmid. These two plasmids don't contain any of the HIV-1 packaging elements (packaging signal and LTR) necessary for encapsidation and/or integration. Expression of helper's proteins is under regulation of the immediate early CMV promoter and transcription termination is provided by the SV40 polyadenylation signal. For different applications we prepared pseudotyped viruses containing the vesicular stomatitis virus glycoprotein (VSV-G), or alternatively, the Ebola glycoprotein (Eb-GP). Recombinant virus generated by three plasmid co-transfection contain the elements required for reverse transcription, integration and gene expression but won't be able to support replication.

Transient cotransfection of 293T cells was carried out by the conventional calcium phosphate technique. Supernatants harvested after 48–60 hr incubation were cleared by passing the cultured media through a 0.45 or 0.22 µm filter and then, virus was concentrated by ultracentrifugation at 100,00×g for 45 min. An alternative concentration procedure involved the use of a 100,000 MW cut-off filter during a conventional centrifugation step. Reverse transcriptase (RT) levels were tested in aliquots harvested before and after concentration as a parameter for viral concentration and in parallel. eGFP expression on 293T cells or in HeLa cells determine to establish the actual transducing units in the final preparation.

Construction of an Inducible HIV-1 Vector

Our single tetracycline-inducible and control bicistronic cassettes were removed from the eukaryotic cloning vector with the appropriate restriction sites and cloned into the SIN vector carrying the tat mutation. In this way, any interference of Tat protein over the internal CMV promoter was avoided.

Construction of a Very Large, Naive, Human sFv Phage Display Library

A large, naive, human sFv library was constructed by performing 80 electroporations of >275 million human V$_H$genes randomly combined with 1.6 million each of V$_{kappa}$- and V$_{lambda}$-gene III fusions in the pFARBER phagemid vector. These ratios were chosen to maintain maximal V$_H$diversity since the majority of binding energy is contributed by V$_H$CDR3. A total of 1.63×10$^{10}$ transformants were isolated. Analysis by restriction enzyme digestion demonstrated an sFv insert efficiency of >92%, yielding a library of 15 billion members. This library was readily rescued with helper phage and infected TG 1 bacteria all contained the expected 800 bp sFv insert. Master vials of the transformed bacterial were aliquoted and frozen as glycerol stocks.

Figure 16:
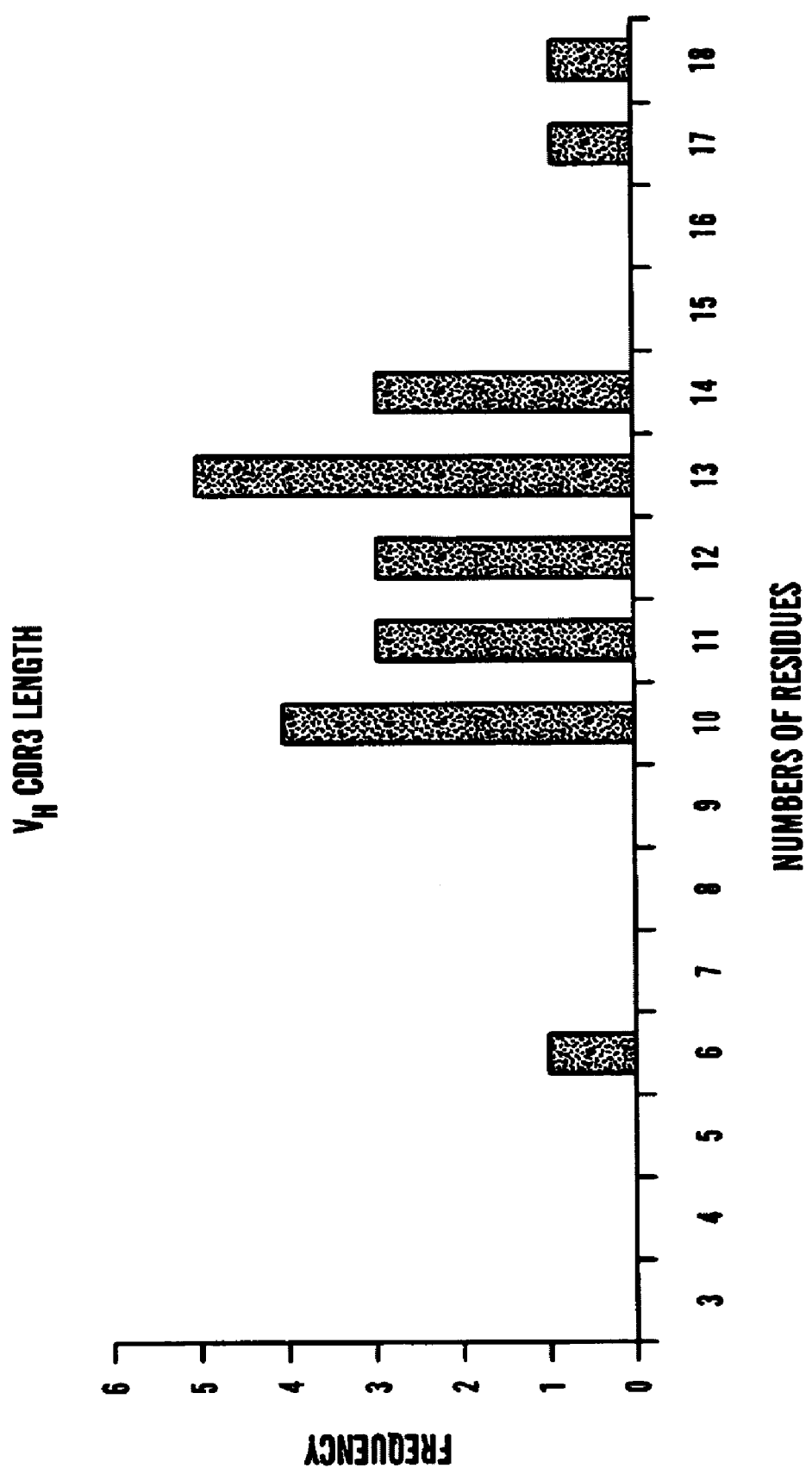
FIG. 16 illustrates that the average length of the diversity segment in VHCDR3 ranges from 6 amino acids to 18 amino acids with the majority of the rearranged VH genes showing CDR3 lengths between 10 and 14 amino acids.
Figure 17:
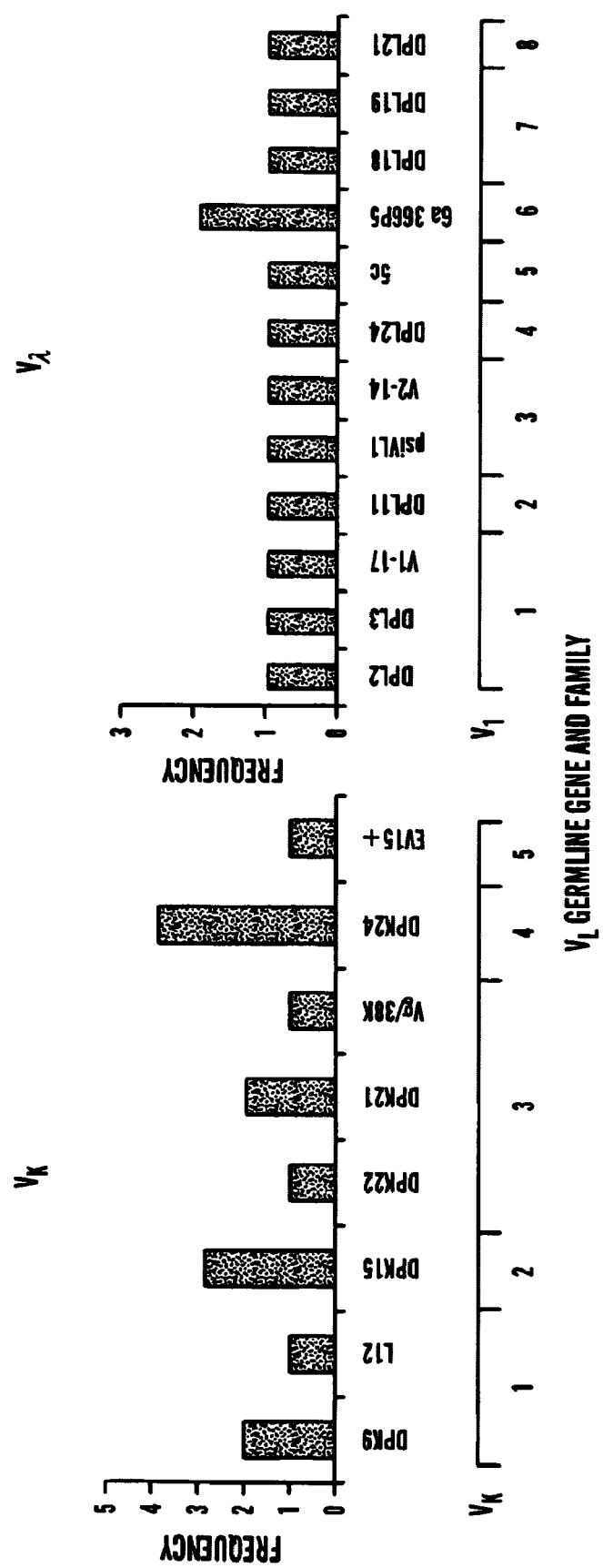
FIG. 17 illustrates eight different Vkappa germline genes that were identified representing five of six different Vkappa families and 12 different Vlambda germline genes were used representing eight of 10 different Vlambda families.

Analysis of Genetic Diversity of the Naive Human sFv Phage Display Library 33 randomly chosen sFvs were DNA sequenced to analyze genetic diversity to identify the V$_H$, D, J$_H$, V$_{kappa}$, J$_{kappa}$, V$_{lambda}$ and J$_{lambda}$ germline gene segments and V$_H$CDR3 length and to create a DFCI database of recovered sFv genes. Analysis of germline gene segments is through "V Base: A database of human immunoglobulin variable region genes. Ian M. Tomlinson, Samuel C. Williams, Simon J. Corbett, Jonathan P. L. Cox and Greg Winter. MRC Center for Protein Engineering, Hills Road, Cambridge, CB2 2QH, UK". The data from these analyses are shown in FIGS. 15-17.

Figure 15:
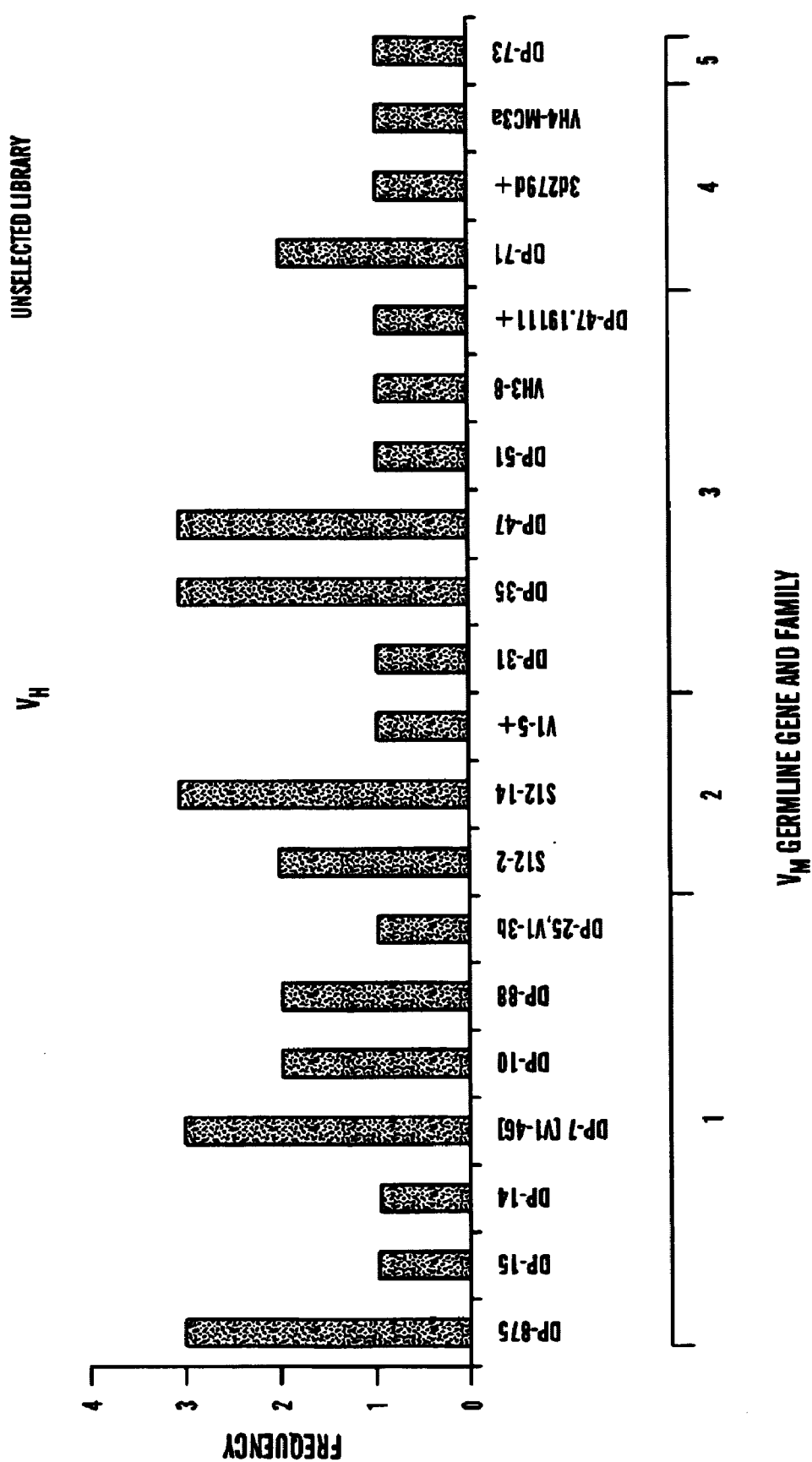
FIG. 15 illustrates the results of human VII germline gene usage for 33 VH genes for which we could make an assignment.

FIG. 15 shows the results of human V$_H$ germline gene usage for 33 V$_H$ genes for which we could make an assignment. The diversity includes 20 different germline genes representing five of seven V$_H$ families. None of the replicate V$_H$ genes (e.g. DP-875, DP-7, S12-14, etc.) are identical to other members that are derived from the same V$_H$ germline gene. Another indication of genetic diversity is the length of the V$_H$CDR3. The data presented in FIG. 16 shows that the average length of this diversity segment ranges from 6 amino acids to 18 amino acids with the majority of the rearranged $V_H$ genes showing CDR3 lengths between 10 and 14 amino acids. This is in excellent agreement with published reports with natural antibodies. Finally, 28 $V_L$ genes were analyzed for $V_{kappa}$ and $V_{lambda}$ germline gene assignment. In humans, these two classes of light chains are used at a frequency of approximately 1:1 unlike mouse where 95% of light chains are kappa family members. As can be seen in FIG. 17, eight different $V_{kappa}$ germline genes were identified representing five of six different $V_{kappa}$ families and 12 different $V_{kappa}$ germline genes were used representing eight of 10 different $V_{lambda}$ families. Again, when replicate $V_L$ germline gene usage occurred somatic point mutations confirmed that the genes were not identical.

Accordingly, we believe there is broad genetic diversity in this very large, naive, human sFv antibody-phage display library. Each of the major heavy and light chain families were represented, but not all of the minor families. The latter finding is most likely due to the small sample size that we have analyzed.

In Vitro Functionality of the Single-Plasmid Inducible System

Figure 3:
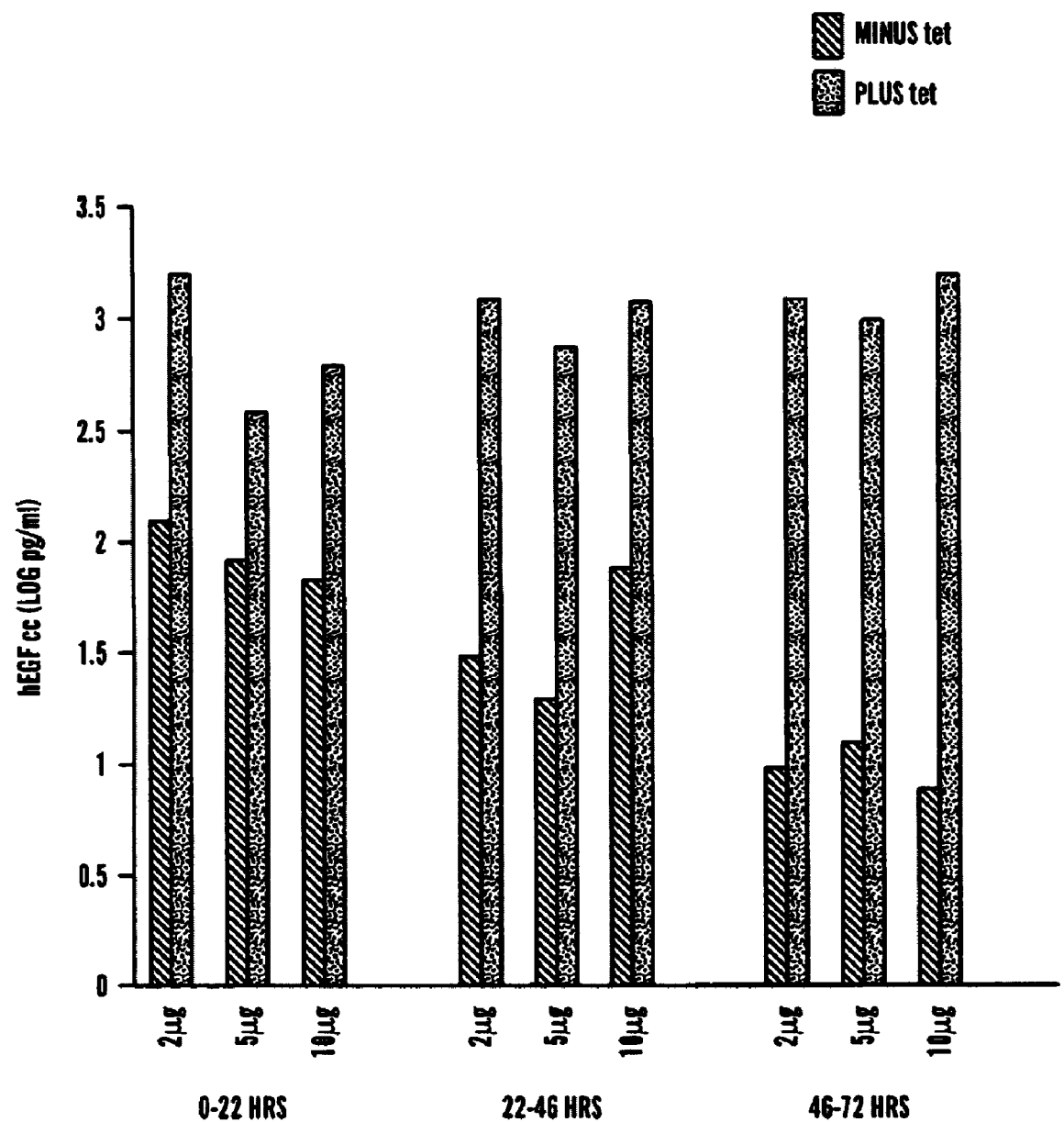
FIG. 3 represents the results obtained from transfecting with the tetracycline-inducible plasmids at various concentrations (2, 5 or 10 µg).

A transfection assay was performed as was described in methods. As internal comparison for our experiment, we included a transfection assay using the two plasmid system described by Yao et al., Human Gene Ther. 9: 1939–1950 (1998). Results obtained co-transfecting pCMtetOhEGF with the control vector, pcDNA3 or the plasmids were consistent with the findings reported in Yao's paper (data not shown). FIG. 3 represents the results obtained after supernatant analysis of Vero cells transfected with the tetracycline-inducible plasmid at various concentrations. There are not significant differences in term of efficiency of our system when 2, 5 or 10 µg of plasmid was used for transfection. As described for the two plasmid system, hEGF expression was reduced in a time-dependent manner. Notably, HEGF expression was repressed and sustained for a period of 72 hrs, reaching about 1,300-fold repression at 46–72 hr post-transfection.

Three genetically modified HIV-1 based vectors (described above) were tested for their ability to infect HeLa cells in vitro. The eGFP was used as reporter gene and gene expression driven from the internal CMV promoter or from the viral promoter itself evaluated by FACS analysis. FIG. 18 shows the results obtained with the 6 constructs. There is no significant reduction in the titers obtained when the original lentiviral vector was self-inactivated or when a significant portion of the gag gene and the first exon of the tat gene were removed. It is important to point out that the reverse transcriptase titers obtained with our preparations don't differ between the different constructions (data not shown). This fact correlates to some previous reports where it has been demonstrated that the integrity of the tat protein is fundamentally required to increase viral transactivation during virus propagation. In our case, a full sequence of the exons 1 and 2 of the tat gene is provided in trans into the packaging construct during transfection, providing the necessary amount of tat protein to produce the virus. In FIG. 15, we can also observe that expression of eGFP can be directed by the wildtype viral promoter (HVPΔEB). Further manipulations of the promoter region such the self-inactivation slightly reduces gene expression driven by the viral promoter but, when the strong trans-activator, tat protein, is not present, could more significant decrease the % of fluorescence. indicating some promoter attenuation.

Transcriptional Control of mRNA Expression by tetR

A polycistronic mRNA of about 2 Kb, encoding the reporter gene as well as the tetR is the result of the initial rounds of gene transcription from both, inducible and control plasmids (FIG. 2). Initial production of tetR by cap-independent translation is mediated through an IRES sequence. The ~500 nucleotides of the IRES element contains the cis-acting elements necessary to recruit the small ribosomal subunits promoting internal initiation of translation of RNA [E. Martinez-Salas, Curr. Opin. Biotechnol. 10: 458–64 (1999)]. Concomitantly with tetR production, transcriptional shut off occurs in the absence of tetracycline. The mechanism can be explained as a high affinity and effective interaction between dimers of tetR and two tandem tetO sequences located between the TATA box and transcription start site of the CMV promoter, resulting in blockage of transcription initiation. When tetracycline (Tet) is added to the system, tetR releases binding to the tetO because of a higher association constant between the repressor and the antibiotic [W. Hinrichs et al., Science 264: 418–420 (1994)]. As a result, high levels of expression can be achieved through activation of the chimeric CMV promoter.

Figure 2B:
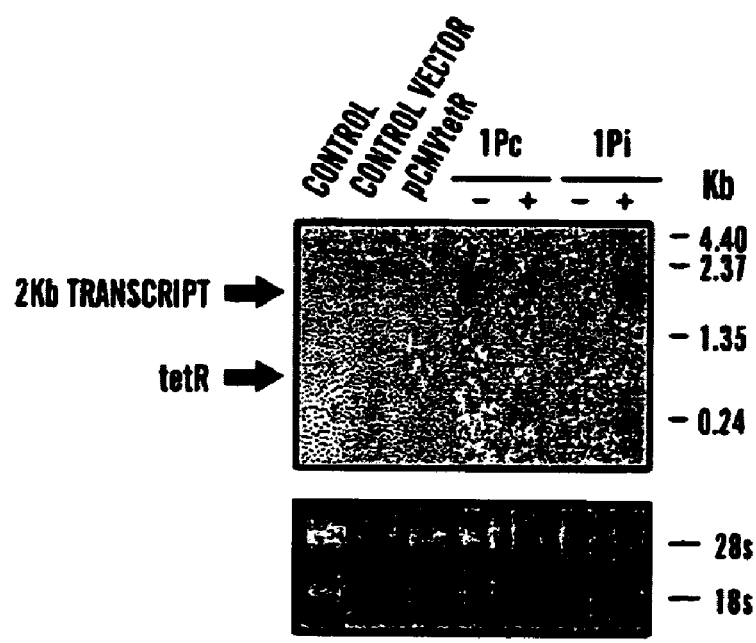

Transcript levels found in transduced VERO cells after 48 hr post-transfection were analyzed by Northern blotting. A radiolabeled tetR probe was used to visualize mRNAs produced from the control and inducible plasmids (underlined in FIG. 2A). Total RNA from non-transfected cells and from cells transfected with an empty control plasmid were considered our negative control (FIG. 2B, lanes 1,2). In parallel, cells were transduced with pcDNAtetR plasmid and its RNA used as positive control of our experiment (lane 3). The probe was able to detect a transcript of about 0.6 Kb corresponding to the mRNA size of the tetR gene. Cells transduced with a one-piece control plasmid (1Pc) showed expression of a higher molecular weight mRNA corresponding to the expected size for our construct. No differences in expression can be noted in the absence or presence of 1 mg/ml tetracycline (FIG. 2B, lanes 4,5). However, transcript levels corresponding to cells transduced with the one-piece inducible cassette (1Pi) showed regulation of expression according to the proposed model (FIG. 2B, lanes 6,7). In the absence of the antibiotic and 48 hours post-transfection, no transcript could be detected. As we described before, a few molecules of bicistronic mRNA need to be synthesized to serve as a mold for cap-independent translation of the repressor. It is possible that the initial mRNA molecules get rapidly degraded from the cell, or that low levels of mRNA are being produced at very basal levels to maintain silenced gene transcription. Another possibility is that the life-span of tetR in the cell is long enough to preserve de-regulation of the system. Total RNA levels are shown in the bottom panel of FIG. 2B, demonstrating that equal amounts of RNA were loaded.

Regulation of hEGF Expression from a Single Cassette

Tight control of gene expression requires a system with high inducibility, specific and dose-dependent response to the inducer, as well as the capability to return to basal levels after the inducer is removed. We tested these three properties of the single cassette by in vitro transfection experiments.

Figure 7:
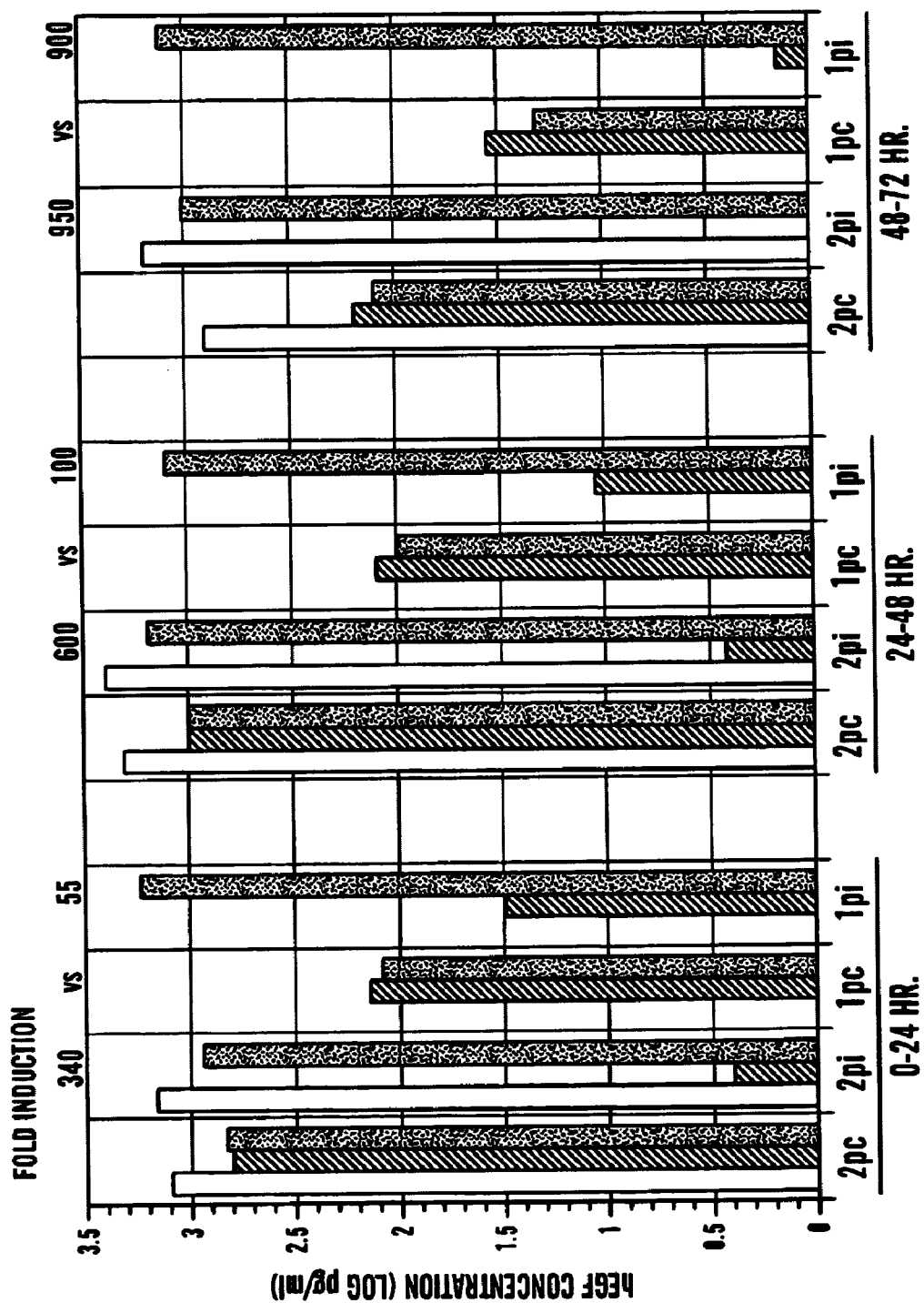
FIG. 7 is a comparison of the regulation of hEGF expression using two separate plasmids or a single control cassette. Vero cells in duplicate, were independently transfected with the 2 plasmid system using 0.5 µg of pCMVtetOhEGF (2Pi) or the non-regulated version pCMVhEGF (2Pc) alone (white bars), or in combination with 2 µg of pcDNAtetR (striped and black bars) or empty vector pcDNA3.1 (−), either in the absence (white and striped bars) or presence of 1 µg/ml of tetracycline (black bars). To test the one piece control (1Pc) and inducible plasmids (1Pi), cells in triplicates were independently transfected with 2.5 µg of the corresponding DNA in the absence (striped bars) or presence (black bars) of the antibiotic. Extracellular medium was collected from the transfected cells at the indicated times and the expression of HEGF was measured by ELISA.

Efficiency. We analyzed the efficiency of our single cassette compare to the previous system described by Yao and collaborators. [F. Yao et al., Human Gene Ther. 9: 1939–1950 (1998)], where the expression control and the regulatory components are present in two separate plasmid. For that purpose, we performed parallel functional studies of the efficiency of both systems by measuring the amount of hEGF secreted into the culture media of transfected VERO cells (FIG. 7). Experimental conditions were similar to those described for the two plasmid system [F. Yao et al., *Human Gene Ther.* 9: 1939–1950 (1998)]. Reporter gene expression was analyzed after harvesting the extracellular medium every 24 hr and measuring the amount of HEGF produced by ELISA. The data obtained using the two plasmid construct were consistent with the results reported previously by Yao et al., *Human Gene Ther.* 9: 1939–1950 (1998). Expression of hEGF from the control plasmid did not exhibit any variation to antibiotic administration. Expression of hEGF from pCMVtetOhEGF was unaffected unless tetR was co-transfected achieving about 340-fold repression during the first 24 hr. increasing up to 600-fold and 950-fold during the two consecutive time points, respectively, in the absence of tetracycline. Similarly, using our single cassette, we observed no difference in hEGF expression levels driven out of the CMV promoter of the 1Pc construct. However, a time-dependent tetR repression was clearly observed using the 1Pi system. 55-fold, 100-fold and 900-fold repression were detected at 0–24 hr, 24–48, and 48–72 hr post-transfection. Both genes were simultaneously expressed from the bi-cistronic mRNA during the first round of transcription until sufficient IRES-mediated tetR synthesis was achieved to block gene activation. Consequently, cap-mediated translation of the first cistron occurred, contributing to higher levels of hEGF production from the 1Pi system compare with the two plasmid system in the absence of tetracycline. We also observed that tetR-mediated repression using the single cassette exhibited a certain delay compared to the results observed using the two plasmid system. The explanation could be that the required levels of tetR are not reached until 48 hr post-transfection, and/or the complete clearance of the initially synthesized hEGF occurs over time. After 48 hr comparable levels of repression were obtained from both systems proving the efficiency of our system.

Figure 8:
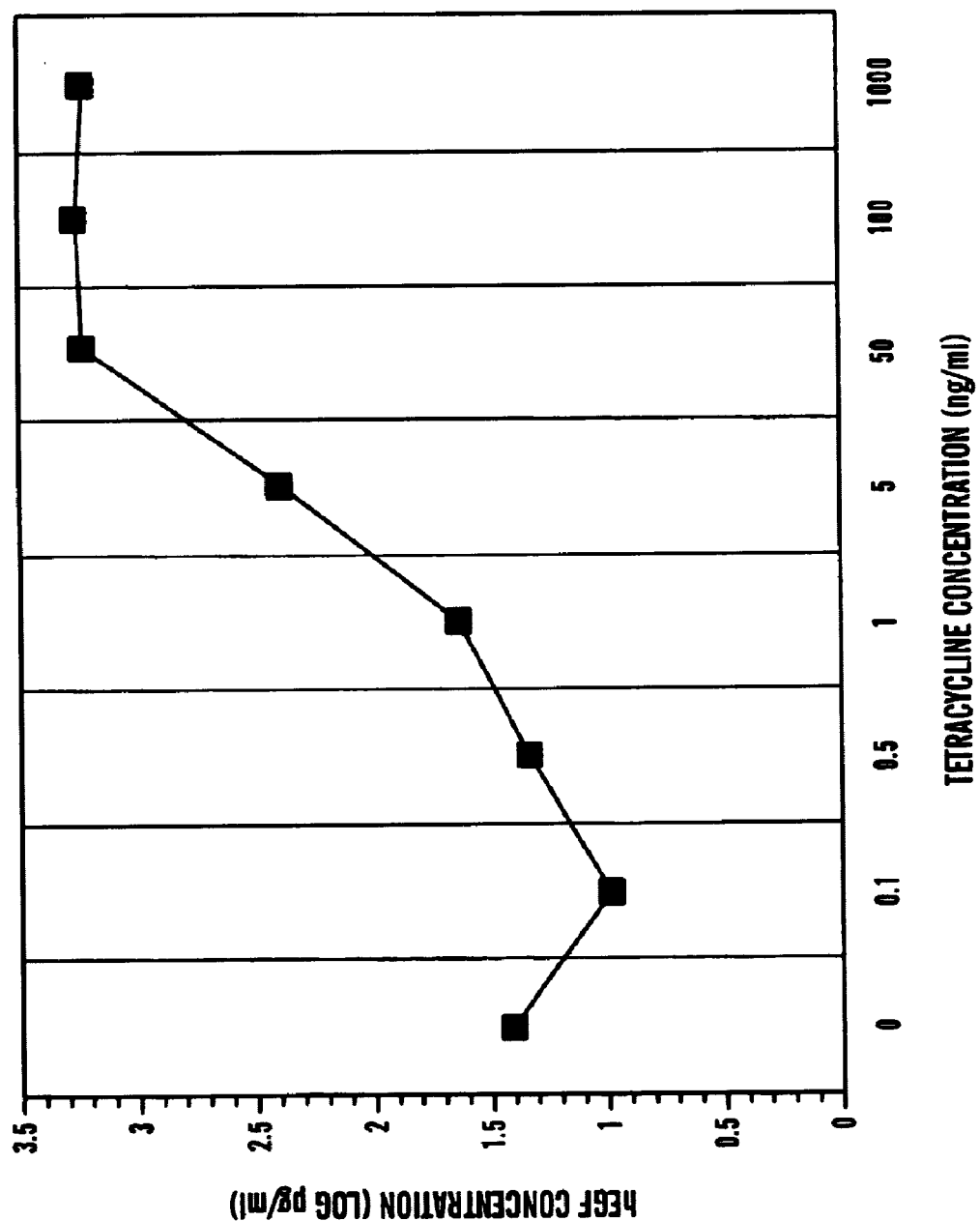
FIG. 8 shows dose-response effects to tetracycline. Vero cells transfected with the 1Pi cassette were treated and grown in the presence of increasing concentration of tetracycline in the culture media. After 48 hr., the amount of HEGF released to the medium was analyzed by ELISA.

Dose-response. Release of tetR-mediated repression was observed after addition of increasing concentrations of tetracycline to the culture media of transfected VERO cells with the 1Pi system (FIG. 8). Full activation of the system was obtained with 50 ng/ml of tetracycline.

Figure 9:
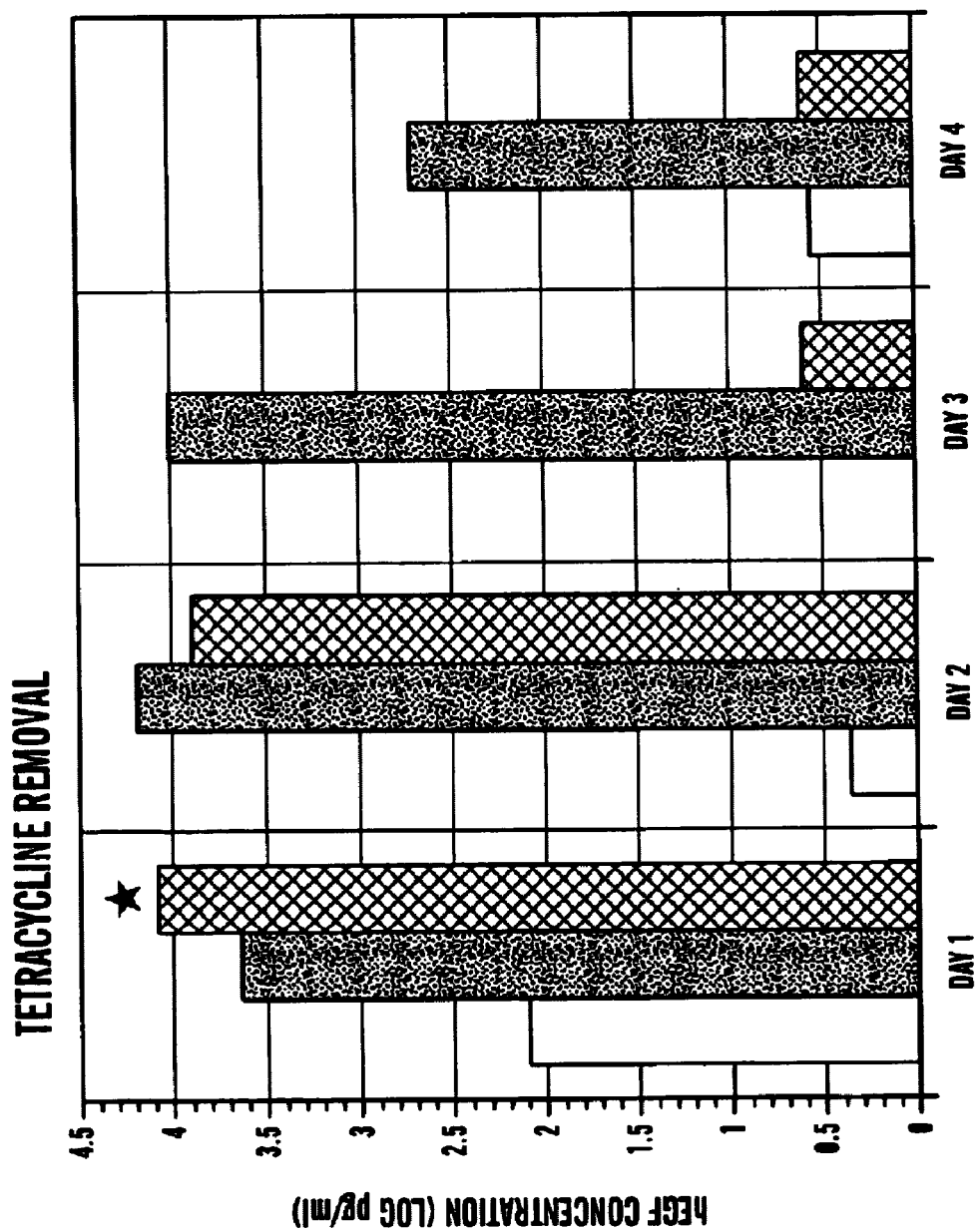
FIG. 9 shows the reversible effects of our single cassette in VERO cells. Transfected cells were cultured in the absence (white bars) or presence of tetracycline during the entire experiment (black bars) or alternatively, after 24 hr. treatment, the cells were maintained in media without the inducer (shaded bars). Culture media was analyzed for hEGF production at the indicated time points.

Reversibility. We have tested the capability of the 1Pi system to respond to tetracycline removal after induction (FIG. 9). Vero cells transfected with the 1Pi construct were incubated in the absence or presence of 1 µg/ml of tetracycline. After 24 hr, a set of cells previously exposed to the inducer were refed with fresh medium lacking tetracycline and the concentration of hEGF was analyzed in the culture media. As shown in FIG. 9, hEGF secretion continued almost unaffected over the next 24 hr but dramatically dropped to basal levels after 48 hr in the absence of tetracycline. Transcription initiation of the hEGF gene in cells previously undergoing gene expression was inhibited, achieving 2,500-fold repression for at least 2 days. Cells that were kept in the uninduced state exhibited a maximum of 10,000-fold repression after 3 days post-transfection.

Figure 10:
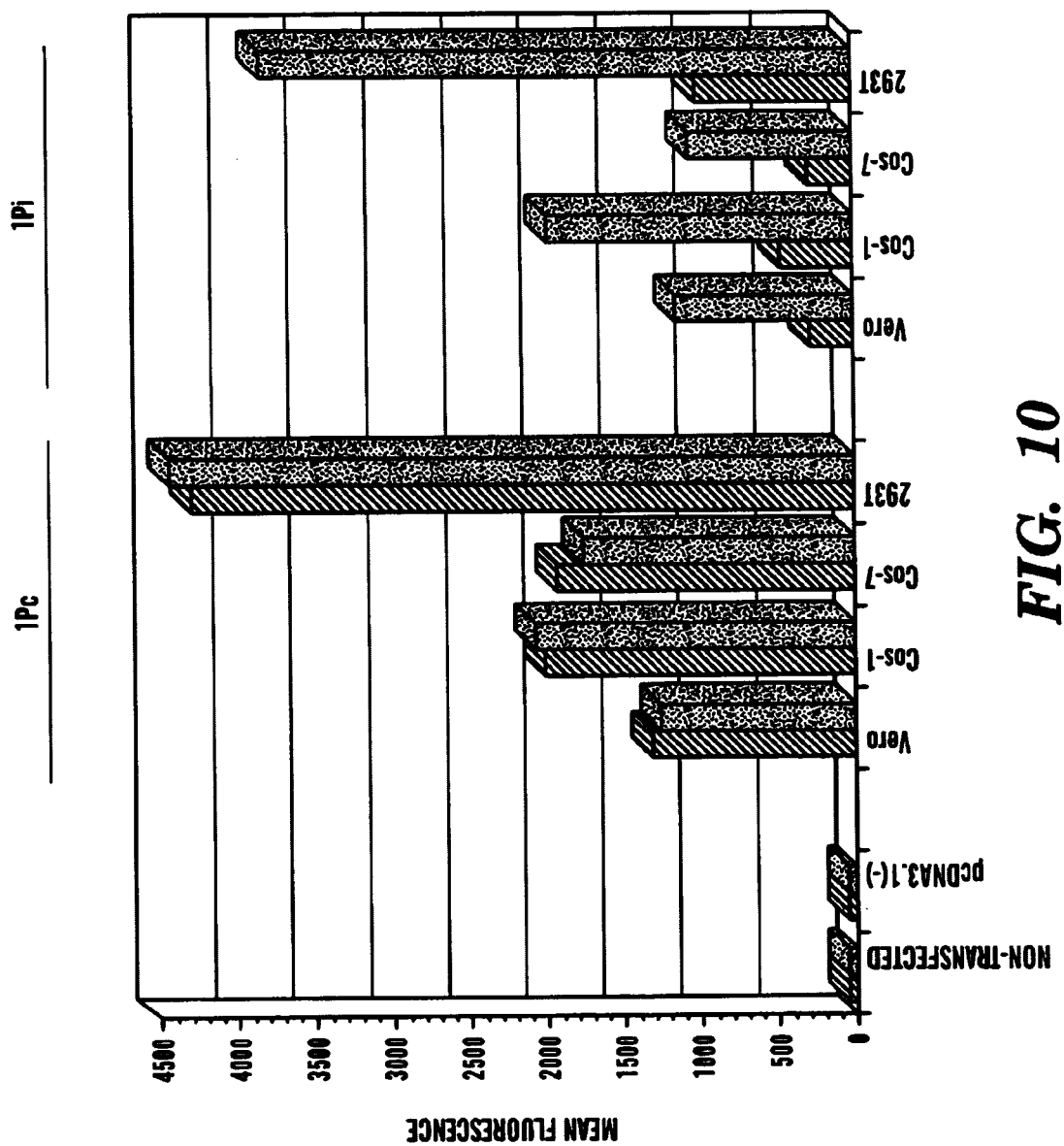
FIG. 10 shows regulation of eGFP expression in different cell lines. Non-transfected and cells transfected either with an empty vector, pcDNA3.1 (−) or with our 1Pc or 1Pi plasmids were analyzed by FACS analysis after 48 hr. posttransfection, to determine endogenous eGFP expression in different cell lines in the absence (striped bars) or presence (black bars) of 1 µg/ml tetracycline.

Regulation of eGFP Expression from a Single Plasmid System in Different Cell Lines The ability of the tetO-bearing CMV promoter to control expression of the reporter gene in cell lines besides the VERO cells was determined. For that purpose, we replaced the HEGF gene from our constructs with the enhanced green fluorescent protein (eGFP) gene and screened diverse cell lines for endogenous expression of the protein using FACS analysis to measure expression of eGFP at different time points (FIG. 10). In all the cases, control cells or cells transfected with an empty vector did not show any significant fluorescence background. (FIG. 10 shows data for VERO cells.) VERO, COS-1, and COS-7 cells exhibited similar levels of eGFP expression from the 1Pc plasmid, as measured by fluorescence intensity. eGFP expression in the human cell line 293T was 2 times higher than in the monkey cell lines. Overall, no variation in terms of mean fluorescence in the absence or presence of the tetracycline was observed. Performance of the control tetO unit was similar between cell lines, reaching 5-fold repression of eGFP intensity in the absence of the tetracycline. The activity of the tetO-bearing CMV promoter varied between cell lines. In particular, higher expression levels as well as background in the absence of tetracycline were observed in the human 293-T cell line; probably due to the presence of the E1A/B gene products from adenovirus, which have been shown to promote the activity of the viral CMV promoter. Similar results were collected after analyzing cells harvested at 24 hr, 48 hr and 72 hr post-transfection (data not shown).

All the cell lines studied exhibited significant background levels of expression in the absence of tetracycline. To examine whether the basal levels of expression were a consequence of leakage of the system or merely caused by slow turnover of the eGFP protein, we used immunohistochemistry to look simultaneously at the production of eGFP (FITC filter) and tetR (PE filter) in transduced VERO cells without or with the addition of tetracycline (FIG. 11). Cap-mediated-eGFP (FIGS. 11A, 11C) and IRES-mediated tetR (FIG. 11B, 11D) production from the 1Pc plasmid remained unaffected in the absence or presence of the inducer. Cytoplasmic and nuclear distribution of the both proteins was observed in different cells. being mostly nuclear for eGFP and mostly cytoplasmic for the repressor. Cells transfected with the 1Pi construct exhibited a different behavior. Although in the absence of tetracycline eGFP protein could be visualized (FIG. 11E), expression of tetR was faintly observed (FIG. 11F). Moreover, when the repression was released by adding tetracycline, eGFP and tetR positive cells were detected (FIGS. 11G, 11H). Therefore, tetR-mediated repression works efficiently in those cells but the long-life and stability of eGFP does not allow us to determine precisely in a short period of time the grade of activation or repression of the system using this marker gene.

Figure 12:
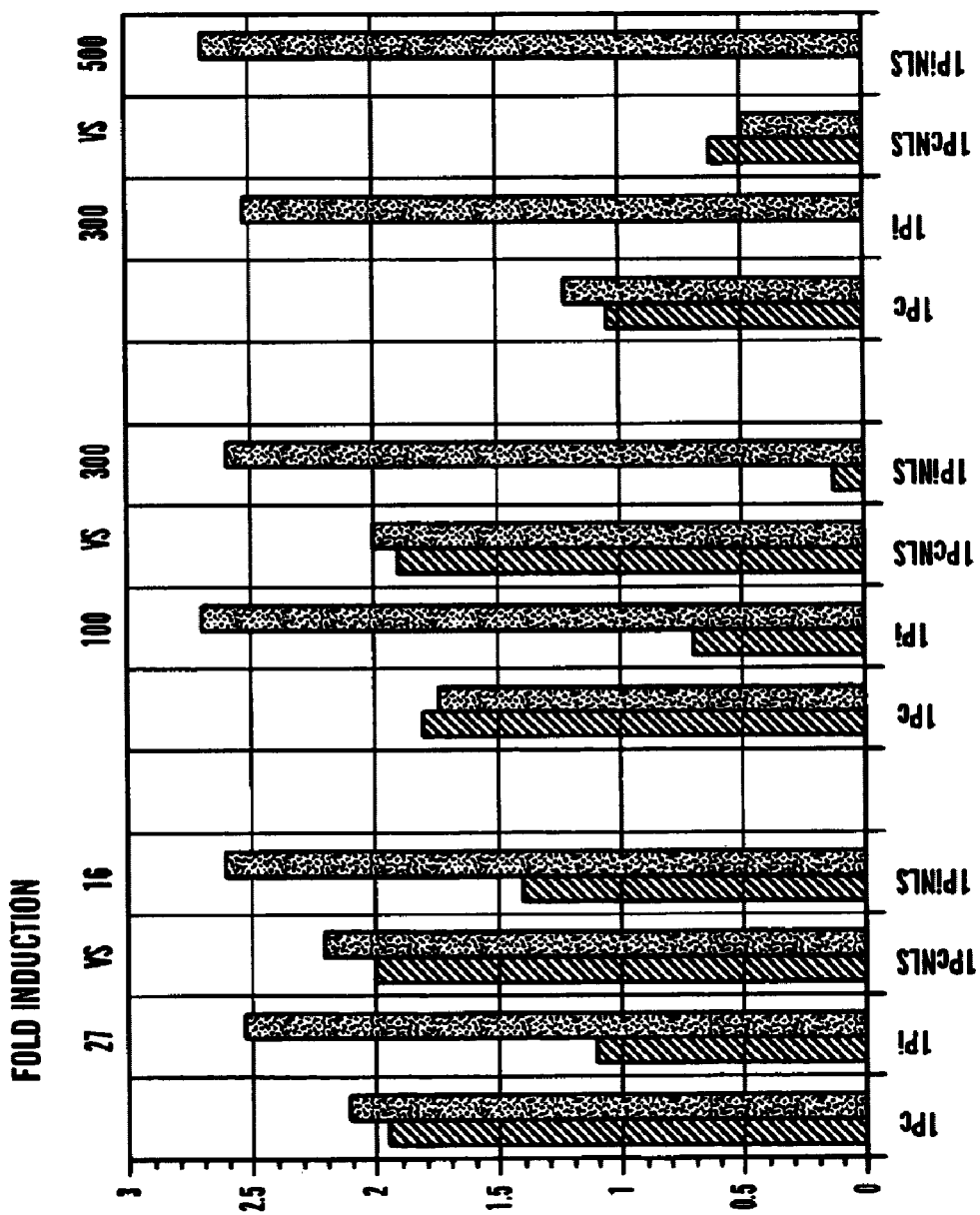
FIG. 12 shows tetR-mediated repression is enhanced by inserting a NLS sequence. Vero cells transfected either with the control (1Pc or 1Pc.NLS) or the inducible (1Pi or 1Pi.NLS) version of our constructs were grow in the absence (striped bars) or presence (black bars) of tetracycline. Aliquots of harvested supernatants were analyzed to determine the amount of hEGF secreted into the culture media.
Figure 13A:
FIGS. 13A–D show immunolocalization of tetR after addition of the NLS sequence. Localization of tetR protein after transfection of VERO cells with different plasmid constructs was performed by conventional immunofluorescence. Cells transfected with a control plasmid (FIG. 13A), the pcDNAtetR plasmid (FIG. 13B), and the 1Pi (FIG. 13C) or 1Pi.NLS.
Figure 13B:
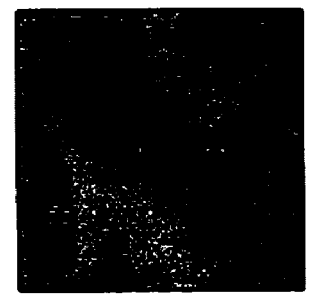
Figure 13C:
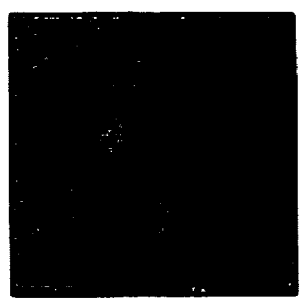
Figure 13D:
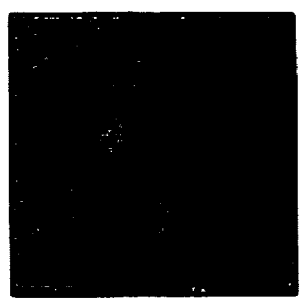

Introduction of a Nuclear Localization Signal Accelerates tetR-Mediated Repression Having observed that tetR distribution is mostly cytoplasmic, a nuclear localization signal (NLS) was introduced at the 3' end of the tetR gene to encourage its import into the nucleus and consequently reinforce the tetR-mediated repression of transcription. FIG. 12 illustrates the results of transient transfection experiments in VERO cells using the 1Pi system and the modified version containing the NLS sequence. Measurement of the HEGF produced and secreted into the medium demonstrated that no significant difference was seen between the plasmids after 24 hours. However, a more rapid tetR-mediated repression was observed after 48 hours with the NLS construct, obtaining 300-fold repression or 3 times higher efficiency of the tetRNLS protein than the untargeted tetR, in the absence of the tetracycline. After 48 hours, 300-fold and 500-fold repression was achieved from the 1Pi and 1PiNLS plasmids respectively. No significant difference in terms of induction of the system was observed between constructs. All constructs containing the wild-type CMV promoter did not show any regulatory effects throughout the experiment.

Distribution of tetR in different constructs was analyzed by immunocytochemistry using the monoclonal antibody against bacterial tetR and detecting the binding using a secondary antibody labeled with FITC (FIG. 13). Cells transfected with an empty vector showed no staining (FIG. 13A). As expected, cells transfected with pcDNAtetR were positive (FIG. 13B). To detect tetR production, cells were treated with tetracycline for 2 days prior to fixation. TetR expression from 1Pi was present in both the cytoplasm and the nucleus (FIG. 13C), while tetRNLS protein was mostly found into the nucleus (FIG. 13D).

Infection of CD8-Depleted Monkey and Human PBMC's Using HIV-1 or SHIV GFP Vectors Cell were infected using VSV-G pseudotyped HIV-1 (67,000 RT/ml) or SHIV (6.000 RT/ml) GFP viruses in the presence of 20 µg/ml of DEAE-dextran for 4 hr. Then, the cells were washed with 1×PBS and refed with fresh media. Green fluorescent gene expression was analyzed 48 hr. post-infection by FACS analysis.

Figure 14:
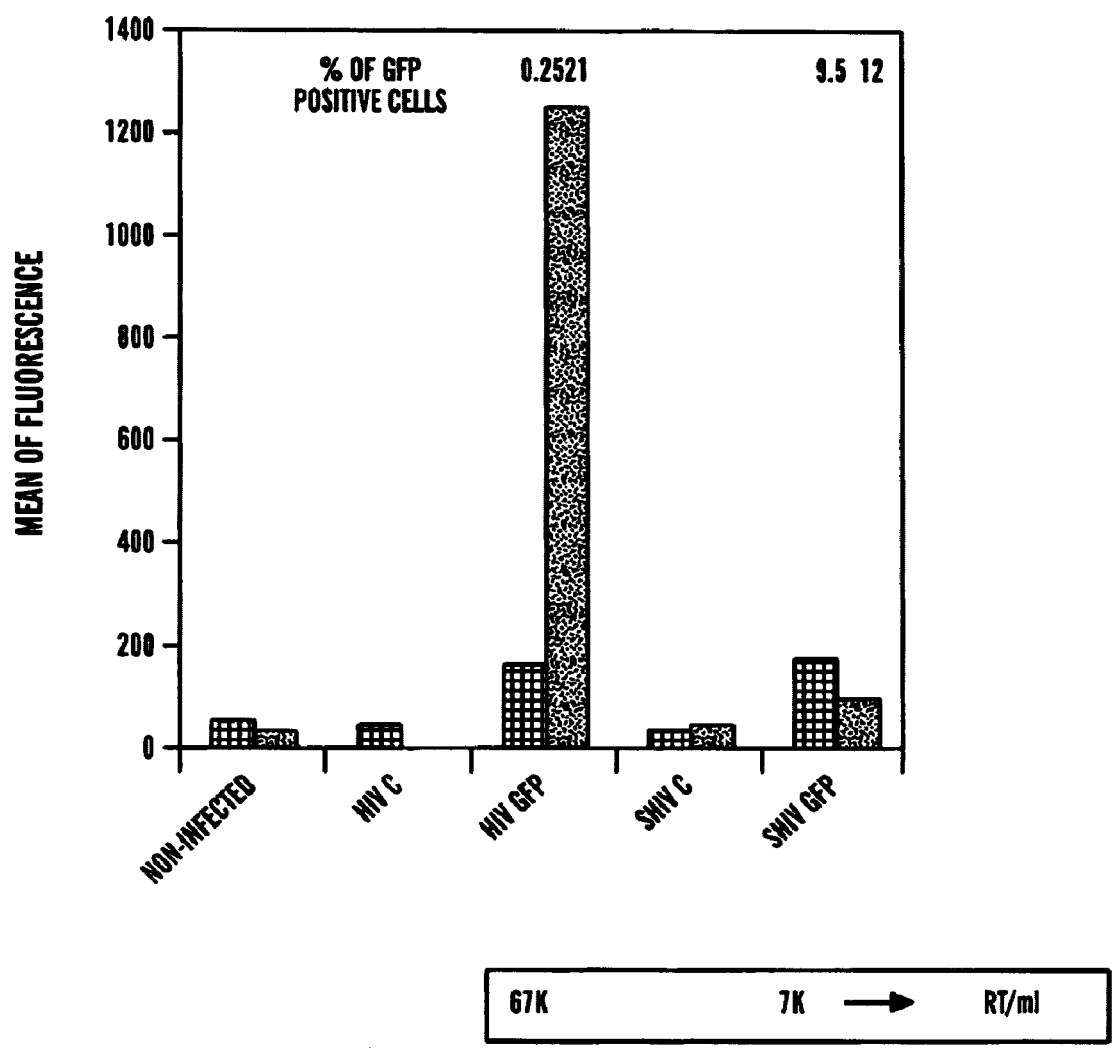
FIG. 14 shows a comparison of infection of monkey CD8-(striped bars) and human CD8-(solid black bars) PBMC's infected by two pseudotyped primate lentivirus (HIV and SHIV)

FIG. 14 shows the results of infection of PPMC's by HIV-1 and SHIV pseudotyped VSV-G. Although GFP expression from infected monkey cells is not as bright as the expression obtained using HIV-1 vectors in human PBMC's, a higher percentage of fluorescent cells could be obtained using the SHIV viruses (about 10% with SHIV vectors versus 0.25% using the HIV-1 vectors). It is important to highlight that the amount of total virus used for infection differs in almost 10-fold. The use of comparable load of virus during infection would provide a better idea about the performance of the SHIV vectors compared to HIV-1 vectors in in vitro experiments using monkey-derived PBMC's.

|              | Monkey CD8-Human CD 8- |      | % of GFP cells/H |      |    |
| ------------ | ---------------------- | ---- | ---------------- | ---- | -- |
| non-infected | 48.5                   | 26   | 0.02             | 1    |    |
| HIV C        | 40                     |      | 0.37             |      |    |
| HIV GFP      | 166                    | 1250 | 0.89             | 21   | 67 |
| SHIV C       | 29.3                   | 40   | 1.23             | 1.85 |    |
| SHIV GFP     | 169                    | 90   | 9.2              | 12   | 7  |

What is claimed is:

1. A vector system comprising a first vector containing a lentiviral gag gene encoding a lentiviral gag protein, wherein the primate lentiviral gag gene is operably linked to a promoter and a polyadenylation sequence;
- a second vector containing an env gene encoding a functional envelope protein, wherein the env gene is operably linked to a promoter and a polyadenylation sequence;
- a lentiviral pol gene encoding a lentiviral pol protein on the first or second vectors or on at least a third vector, wherein said lentiviral pol gene is operably linked to a promoter and a polyadenylation sequence;
- a) wherein said at least first, second and third vectors do not contain sufficient nucleotides to encode the lentiviral gag and pol and the envelope protein on a single vector; and
- b) wherein said vectors do not contain nucleotides of the lentiviral genome referred to as a packaging segment to effectively package lentiviral RNA; and
- c) wherein the lentiviral proteins and the envelope protein when expressed in combination form a lentivirus virion containing an envelope protein around a lentiviral capsid;
- a packaging vector containing a nucleic acid sequence encoding a desired molecule, wherein the desired molecule is an angiogenic protein, where the nucleic acid sequence is operably linked to an inducible promoter and a lentiviral packaging sequence including portions of lentiviral long terminal repeat (LTR) sequences necessary to package the lentiviral RNA into the lentiviral virion; and
- d) wherein said packaging vector contains a deletion of the U3 portion of the lentiviral LTR sufficient to inactivate the lentiviral promoter and/or do not express a tat protein that has transactivating functions; wherein the envelope protein is encoded by an Ebola virus gene; and wherein the lentivirus is the human immunodeficiency virus.

2. The vector system of claim 1, wherein the angiogenic protein is VEGF.

3. A method of delivering an angiogenic protein to a vascular endothelial cell which comprises administering a particle produced by the vector system of claim 1.

* * * * *

SEQUENCE LISTING

```
<160> NUMBER OF SEQ ID NOS: 3

<210> SEQ ID NO 1
<211> LENGTH: 24
<212> TYPE: DNA
<213> ORGANISM: Simian virus

<400> SEQUENCE: 1
gatccaaaaa agaagagaaa ggta                                         24

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      ER retention sequence

<400> SEQUENCE: 2

Lys Asp Glu Leu
  1

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      ER retention sequence
```

```
<400> SEQUENCE: 3

Ser Glu Lys Asp Glu Leu
  1               5
```